(12) United States Patent
Morgan

(10) Patent No.: US 11,832,892 B2
(45) Date of Patent: Dec. 5, 2023

(54) NAVIGATION SYSTEMS FOR COMMUNICATING TRACKER STATUS CONDITIONS

(71) Applicant: MAKO Surgical Corp., Ft. Lauderdale, FL (US)

(72) Inventor: Jonathan Mark Morgan, Biscayne Park, FL (US)

(73) Assignee: MAKO Surgical Corp., Weston, FL (US)

(*) Notice: Subject to any disclaimer, the term of this patent is extended or adjusted under 35 U.S.C. 154(b) by 570 days.

(21) Appl. No.: 16/924,643

(22) Filed: Jul. 9, 2020

(65) Prior Publication Data

US 2021/0007809 A1 Jan. 14, 2021

Related U.S. Application Data

(60) Provisional application No. 62/872,489, filed on Jul. 10, 2019.

(51) Int. Cl.
*A61B 34/20* (2016.01)
*A61B 34/10* (2016.01)
*A61B 34/30* (2016.01)
*F21Y 115/10* (2016.01)

(52) U.S. Cl.
CPC .............. *A61B 34/20* (2016.02); *A61B 34/10* (2016.02); *A61B 34/30* (2016.02); *A61B 2034/2051* (2016.02); *A61B 2034/2055* (2016.02); *F21Y 2115/10* (2016.08)

(58) Field of Classification Search
CPC ......... A61B 34/20; A61B 34/10; A61B 34/30; A61B 2034/2051; A61B 2034/2055; F21Y 2115/10
See application file for complete search history.

(56) References Cited

U.S. PATENT DOCUMENTS

| 7,725,162 | B2 | 5/2010 | Malackowski et al. |
| 8,010,180 | B2 | 8/2011 | Quaid et al. |
| 8,753,346 | B2 | 6/2014 | Suarez et al. |
| 8,979,859 | B2 | 3/2015 | Leparmentier et al. |
| 9,008,757 | B2 | 4/2015 | Wu |
| 9,119,655 | B2 | 9/2015 | Bowling et al. |
| 2006/0072124 | A1 | 4/2006 | Smetak et al. |
| 2006/0140464 | A1 | 6/2006 | Feilkas et al. |

(Continued)

FOREIGN PATENT DOCUMENTS

WO 2010055193 A1 5/2010

*Primary Examiner* — Joel Lamprecht
(74) *Attorney, Agent, or Firm* — Howard & Howard Attorneys PLLC

(57) ABSTRACT

A navigation system is disclosed which comprises a tracker having a trackable feature, a localizer configured to track states of the trackable feature within a field of view, an illumination assembly operable to direct light within the field of view, and a controller coupled to the localizer and to the illumination assembly. The controller is configured to receive the tracked states from the localizer, to determine a status condition of the tracker based on the tracked states received from the localizer, and to control the illumination assembly to direct light at the tracker such that light reflected by the tracker from the illumination assembly is visible to a user of the navigation system to communicate the status condition of the tracker.

20 Claims, 21 Drawing Sheets

(56) References Cited

U.S. PATENT DOCUMENTS

| | | | |
|---|---|---|---|
| 2009/0275826 A1 | 11/2009 | Enzerink et al. | |
| 2009/0317002 A1 | 12/2009 | Dein | |
| 2017/0245945 A1* | 8/2017 | Zuhars | A61B 90/39 |
| 2017/0258535 A1 | 9/2017 | Crawford et al. | |
| 2018/0023946 A1 | 1/2018 | Elliot | |
| 2018/0185113 A1 | 7/2018 | Gregerson et al. | |
| 2019/0290370 A1 | 9/2019 | Brummund et al. | |
| 2020/0329226 A1* | 10/2020 | Medal | A61B 34/20 |

* cited by examiner

NAVIGATION SYSTEMS FOR COMMUNICATING TRACKER STATUS CONDITIONS

CROSS-REFERENCE TO RELATED APPLICATIONS

The subject application claims priority to U.S. Provisional Patent Application No. 62/872,489, filed Jul. 10, 2019, the contents of which are incorporated by reference in their entirety.

BACKGROUND

Navigation systems are frequently utilized in connection with hand-held surgical tools and/or surgical robotics to assist medical professionals in carrying out conventional surgical procedures with enhanced precision and control. In general terms, the navigation system affords the ability to determine the position and orientation of portions of the patient's anatomy adjacent to a surgical site relative to tracked tools, instruments, end effectors, and the like.

To this end, one or more trackers are generally affixed firmly to portions of the patient's anatomy, and trackers are similarly integrated into or otherwise attached to tools, instruments, and end effectors utilized during a surgical procedure. A localizer tracks states of trackable features of each tracker to determine its relative position and orientation within a field of view. While a number of different types of navigation systems are known in the related art, trackers can generally be characterized as either "active" or "passive" depending, respectively, on the presence or absence of a power source coupled to the tracker. By way of example, "active trackers" may comprise an on-board battery that is used to provide power to light emitting diodes, electromagnetic emitters, radio emitters, and the like that serve as trackable features monitored by the localizer, as well as other electrical components such as inertial sensors. On the other hand, "passive trackers" may comprise trackable features that do not require an on-board power source, such as reflectors and/or specific structural features, shapes, and patterns monitored by the localizer.

Irrespective of the specific configuration of the navigation system, interrupting or impeding the localizer's ability to monitor trackers can result in disadvantageous delays or errors during the surgical procedure. For example, with optical-based navigation systems, obscuring the localizer's line-of-sight to the trackable features of a tracker will impede the navigation system's ability to accurately track states of that tracker. In such instances, a change in the tracker's status is generally communicated to medical professionals via audible or visual alerts, either locally at the tracker (e.g., via a status light for "active" trackers) and/or remote from the tracker (e.g., on a display screen). Accordingly, delays during the surgical procedure may be caused as medical professionals remove obstructions, verify tracker operation, and the like, which is further complicated when multiple trackers are utilized simultaneously. Moreover, depending on the specific configuration of the navigation system (e.g., those configured to monitor passive trackers), a surgeon may have to direct their attention away from the surgical site in order to verify tracker status by, for example, visually checking a display screen to confirm a visual alert, interrupting operation of a surgical tool to confirm an audible alert, and the like.

There remains a need in the art for a navigation system which overcomes at least the deficiencies described above.

SUMMARY

This Summary introduces a selection of concepts in a simplified form that are further described below in the Detailed Description. This Summary is not intended to limit the scope of the claimed subject matter and does not necessarily identify each and every key or essential feature of the claimed subject matter.

The present disclosure provides a navigation system comprising a tracker having a trackable feature, a localizer configured to track states of the trackable feature within a field of view, an illumination assembly operable to direct light within the field of view, and a controller coupled to the localizer and to the illumination assembly. The controller is configured to receive the tracked states from the localizer, to determine a status condition of the tracker based on the tracked states received from the localizer, and to control the illumination assembly to direct light at the tracker such that light reflected by the tracker from the illumination assembly is visible to a user of the navigation system to communicate the status condition of the tracker.

The present disclosure provides a surgical system comprising a tracker having a trackable feature, a localizer configured to track states of the trackable feature within a field of view, an illumination assembly operable to direct light within the field of view, and a controller coupled to the localizer and to the illumination assembly. The controller is configured to receive the tracked states from the localizer, to determine a system condition of the surgical system based on the tracked states received from the localizer, and to control the illumination assembly to direct light at the tracker such that light reflected by the tracker from the illumination assembly is visible to a user of the surgical system to communicate the system condition.

A method of operating the navigation system is also described. The navigation system comprises a tracker having a trackable feature, a localizer configured to track states of the trackable feature within a field of view, an illumination assembly operable to direct light within the field of view, and a controller coupled to the localizer and to the illumination assembly. The controller is configured to perform the steps of: receiving the tracked states from the localizer, determining a status condition of the tracker based on the tracked states received from the localizer, and controlling the illumination assembly to direct light at the tracker such that light reflected by the tracker from the illumination assembly is visible to a user of the navigation system to communicate the status condition of the tracker.

Other features and advantages of the present disclosure will be readily appreciated, as the same becomes better understood, after reading the subsequent description taken in conjunction with the accompanying drawings.

DETAILED DESCRIPTION

Figure 1:
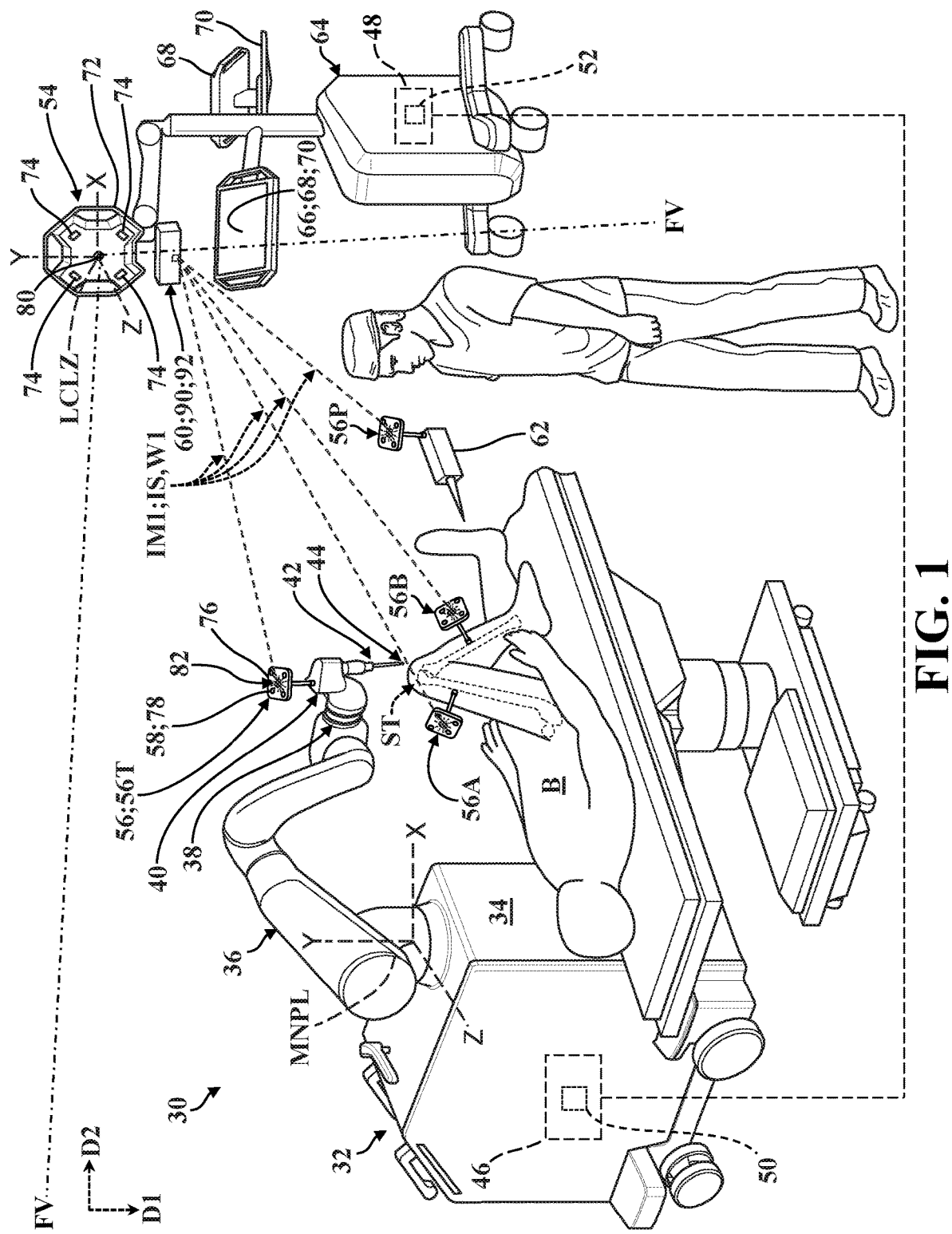
FIG. 1 is a perspective view of a surgical system comprising a surgical robot with a robotic arm supporting an end effector to which a tool is supported adjacent to a surgical site on a patient's body, and shown with a navigation system according to embodiments of the present disclosure comprising trackers, a localizer, and an illumination assembly directing light at the trackers to communicate status conditions of the trackers to a user.

Referring now to the drawings, wherein like numerals indicate like or corresponding parts throughout the several views, navigation systems and techniques are described for communicating the status of one or more trackers utilized with a surgical system 30. One non-limiting example of a surgical system 30 is shown in FIG. 1. In this example, the surgical system 30 comprises a surgical robot 32. Although a robotic system is shown in FIG. 1, the navigation system and techniques described herein can be utilized with any other type of surgical system that utilizes trackers for tracking the pose of objects in the operating room. Such systems may include, but are not limited to, hand-held systems (robotic or non-robotic), table mounted systems, imaging systems, or any combination thereof.

In this example, the surgical robot 32 has a base 34, a robotic arm 36, and a coupler 38. As is described in greater detail below, the robotic arm 36 is supported by the base 34 and is configured to move, drive, maintain, or otherwise control the position and/or orientation of the coupler 38 relative to the base 34 during use. The coupler 38 is adapted to releasably secure an end effector 40 which, in turn, supports a tool, generally indicated at 42. The tool 42 is configured to support, position, or otherwise facilitate driving a workpiece, depicted generically at 44 in FIG. 1, at a surgical site ST on a patient's body B. Thus, the surgical robot 32 moves the workpiece 44, the tool 42, and the end effector 40 via the robotic arm 36 to, among other things, assist medical professionals in carrying out various types of surgical procedures with precise control over movement and positioning of the end effector 40, the tool 42, and the workpiece 44. One exemplary arrangement of the robotic arm 36 is described in U.S. Pat. No. 9,119,655, entitled, "Surgical Robotic arm Capable of Controlling a Surgical Instrument in Multiple Modes," the disclosure of which is hereby incorporated by reference in its entirety. Another exemplary arrangement of robotic arm 36 is described in U.S. Pat. No. 8,010,180, entitled, "Haptic Guidance System and Method," the disclosure of which is hereby incorporated by reference in its entirety. The robotic arm 36 and other portions of the surgical robot 32 may be arranged in alternative configurations.

While the workpiece 44 is generically depicted as an "energy applicator" in FIG. 1, the end effector 40, the tool 42, and/or the workpiece 44 could be of a number of different styles, types, and/or configurations, depending on the specific surgical procedure being performed. By way of non-limiting example, surgical procedures such as total hip arthroplasty routinely involve the use of multiple tools 42 to facilitate approaching the surgical site ST, preparing the surgical site ST, and/or installing implants (e.g., prosthetic components), and the like at the surgical site ST. In this illustrative example, one tool 42 could be a reamer used to facilitate preparing the acetabulum by driving a workpiece 44 realized as a reamer head (not shown in detail), and another tool 42 could be an impactor used to facilitate implanting a workpiece 44 realized as a prosthesis (not shown). The Applicant has described these types of reaming, preparing, and impaction processes in greater detail in U.S. Pat. Nos. 8,979,859 and 8,753,346, the disclosures of which are hereby incorporated by reference in their entirety. While the present disclosure describes various orthopedic procedures (e.g., involving hip joints, knee joints, and the like), the subject matter described herein may be applicable to other joints in the patient's body B, such as, for example, shoulders, elbows, wrists, spines, knees, ankles, and the like.

The surgical system 30 is able to monitor, track, and/or determine changes in the relative position and/or orientation of one or more parts of the surgical robot 32, the robotic arm 36, the end effector 40, the tool 42, and/or the workpiece 44, as well as various parts of the patient's body B and other surgical tools and/or instruments, within or relative to a common coordinate system by utilizing various types of trackers (e.g., multiple degree-of-freedom optical, inertial, radio, and/or ultrasonic sensing devices), navigation systems (e.g., machine vision systems, charge coupled device cameras, tracker sensors, surface scanners, and/or range finders), anatomical computer models (e.g., patient-specific computer topography scans, magnetic resonance imaging scans, X-ray scans, and the like), data from previous surgical procedures and/or previously-performed surgical techniques (e.g., intra-operatively-recorded data acquired during tissue manipulation), and the like. To these ends, and as is described in greater detail below, the surgical system 30 generally comprises a control system 46 and a navigation system 48 which cooperate to facilitate positioning and orientating the workpiece 44 relative to the surgical site ST via the robotic arm 36 of the surgical robot 32. The control system 46 comprises an arm controller 50, and the navigation system 48 comprises a navigation controller 52. The controllers 50, 52 may be realized as computers, processors, control units, and the like, and may be discrete components, may be integrated, and/or may otherwise share hardware.

The surgical system 30 employs the control system 46 to, among other things, articulate the robotic arm 36, facilitate driving the tool 42, and the like. Here, the arm controller 50 of the control system 46 is configured to articulate the robotic arm 36 by driving various actuators, motors, and the like disposed at joints of the robotic arm 36 (not shown). The arm controller 50 also gathers sensor data from various sensors such as encoders located along the robotic arm 36 (not shown). Because the specific geometry of each of the components of the surgical robot 32, end effector 40, and tool 42 are known, these sensor data can be used by the arm controller 50 to reliably adjust the position and/or orientation of the tool 42 within a manipulator coordinate system MNPL (see FIG. 1). The manipulator coordinate system MNPL has an origin, and the origin is located relative to the robotic arm 36. One example of this type of manipulator coordinate system MNPL is described in U.S. Pat. No. 9,119,655, entitled "Surgical Robotic Arm Capable of Controlling a Surgical Instrument in Multiple Modes," previously referenced.

The surgical system 30 employs the navigation system 48 to, among other things, track movement of various objects such as the tool 42 and parts of the patient's body B (e.g., bones located at or adjacent to the surgical site ST). To this end, the navigation system 48 comprises a localizer 54 configured to sense the position and/or orientation of trackers 56 fixed to objects within a localizer coordinate system LCLZ. More specifically, each tracker 56 comprises one or more trackable features 58, and the localizer 54 is configured to track states TS of the trackable features 58 within a field of view FV. The navigation system 48 of the present disclosure also comprises an illumination assembly, generally indicated at 60, that is operable to direct light within the field of view FV. The navigation controller 52 is coupled to the localizer 54 and the illumination assembly 60 and is configured to: receive the tracked states TS from the localizer 54, to determine a status condition SC of one or more trackers 56 and/or a system condition MC of the surgical system 30 based on the tracked states TS received from the localizer 54, and to control the illumination assembly 60 to direct light LT at trackers 56 such that light reflected by the one or more trackers 56 from the illumination assembly 60 is visible to a user (e.g., a surgeon) of the navigation system 48 to communicate the respective status condition SC of the one or more trackers 56 and/or the system condition MC of the surgical system 30. Each of the components introduced above will be described in greater detail below.

As noted above, the navigation controller 52 is disposed in communication with the localizer 54, and gathers position and/or orientation data for each tracker 56 sensed within the field of view FV of the localizer 54 in the localizer coordinate system LCLZ. The localizer 54 can sense the position and/or orientation of multiple trackers 56 to track correspondingly multiple objects within the localizer coordinate system LCLZ. By way of example, and as is depicted in FIG. 1, trackers 56 may comprise a pointer tracker 56P, a tool tracker 56T, a first patient tracker 56A, a second patient tracker 56B, and/or an illumination assembly tracker 56I (see FIGS. 9A-9C), as well as additional patient trackers and/or other types of patient trackers such as ancillary trackers 56N (see FIGS. 10A-10B), trackers for additional medical and/or surgical tools, and the like. In FIG. 1, the pointer tracker 56P is firmly affixed to a pointer tool 62, the tool tracker 56T is firmly affixed to the end effector 40, the first patient tracker 56A is firmly affixed to the patient's right femur adjacent to the surgical site ST, and the second patient tracker 56B is firmly affixed to the patient's right tibia adjacent to the surgical site ST. The pointer tracker 56P could be fixed to the pointer tool 62 in different ways, such as by integration into the pointer tool 62 during manufacture or by releasable attachment to the pointer tool 62. Similarly, the tool tracker 56T could be fixed to the end effector 40 in different ways, such as by integration into the end effector 40 during manufacture or by releasable attachment to the end effector 40. The patient trackers 56A, 62B are firmly affixed to different bones in the patient's body B, such as by threaded engagement, clamping, or by other techniques. Various trackers 56 may be firmly affixed to different types of tracked objects (e.g., discrete bones, tools, pointers, and the like) in a number of different ways.

The position and/or orientation (e.g., "pose") of the trackers 56 relative to the objects to which they are attached can be determined by known registration techniques, such as point-based registration in which the pointer tool 62 is used to touch off on bony landmarks on bone or to touch off on several points across the bone for surface-based registration. Any suitable registration technique can be employed to correlate the pose of the patient trackers 56A, 56B to the patient's anatomy (e.g., each bone). Other types of registration are also possible, such as by using patient trackers 56A, 56B with mechanical clamps that attach to bone and have tactile sensors (not shown) to determine a shape of bone to which the clamp is attached. The shape of the bone can then be matched to a 3D model for registration. In some embodiments, multiple trackers could be attached to the same portion of the patient's anatomy. For example, and as is depicted in the representative embodiment illustrated in FIGS. 10A-10B, a first patient tracker 58A and an ancillary tracker 58N could both be coupled to the same bone (e.g., the femur, the tibia, the acetabulum, or other bones). Other configurations are contemplated.

Tracked states TS, such as for example position and/or orientation data associated with trackable features 58 of one or more trackers 56, may be gathered, determined, or otherwise handled by the navigation controller 52 using any suitable registration/navigation techniques to determine coordinates of each tracker 56 within the localizer coordinate system LCLZ. These coordinates are communicated to the control system 46 to, among other things, facilitate navigation of hand-held surgical tools (not shown) and/or articulation of the robotic arm 36, as described in greater detail below. As used herein, the term "tracked state" includes, but is not limited to, data which represents or defines the position and/or orientation of a tracked object, and/or equivalents or derivatives of the position and/or orientation. For example, a tracked state TS may be a pose of the tracked object, and may include linear data, angular velocity data, and the like. Furthermore, and as is described in greater detail below, tracked states TS may also comprise or otherwise represent data associated with the status condition SC of one or more trackers 56, as well as a system condition MC of the surgical system 30, as described in greater detail below. Other configurations are contemplated.

In the representative example illustrated in FIG. 1, the arm controller 50 is operatively attached to the surgical robot 32, and portions of the navigation system 48 including the navigation controller 52, the localizer 54, and the illumination assembly 60 are supported on a mobile cart 64 which is movable relative to the base 34 of the surgical robot 32. The mobile cart 64 also supports a user interface, generally indicated at 66, to facilitate operation of the surgical system 30 by displaying information to, and/or by receiving information from, the surgeon or another user. The user interface 66 is disposed in communication with the navigation system 48 and/or the control system 46, and may comprise one or more output devices 68 (e.g., monitors, indicators, display screens, and the like) to present information to the user (e.g., images, video, data, a graphics, navigable menus, and the like), and one or more input devices 70 (e.g., buttons, touch screens, keyboards, mice, gesture or voice-based input devices, and the like). One type of mobile cart 64 and user interface 66 is described in U.S. Pat. No. 7,725,162, entitled "Surgery System," the disclosure of which is hereby incorporated by reference in its entirety.

In some examples, the surgical system 30 is capable of displaying a virtual representation of the relative positions and orientations of tracked objects to the surgeon or other users of the surgical system 30, such as with images and/or graphical representations of the bones and the tool 42 presented on one or more output devices 68 (e.g., a display screen). The arm controller 50 and/or navigation controller 52 may also utilize the user interface 66 to display instructions or request information such that the surgeon or other users may interact with the control system 46 to facilitate articulation of the robotic arm 36. Other configurations are contemplated.

Because the mobile cart 64 and the base 34 of the surgical robot 32 can be positioned relative to each other and also relative to the patient's body B, one or more components of the surgical system 30 (e.g., the controllers 50, 52) may transform the coordinates of each tracker 56 from the localizer coordinate system LCLZ into the manipulator coordinate system MNPL, or vice versa, so that articulation of the robotic arm 36 can be performed based at least partially on the relative positions and orientations of each tracker 56 within a common coordinate system (e.g., the manipulator coordinate system MNPL or the localizer coordinate system LCLZ). Coordinates within the localizer coordinate system LCLZ can be transformed into coordinates within the manipulator coordinate system MNPL, and vice versa, using a number of different coordinate system transformation techniques.

The control system 46 and the navigation system 48 can cooperate to facilitate control over the position and/or orientation of the tool 42 in different ways. By way of example, in some examples, the arm controller 50 is configured to control the robotic arm 36 (e.g., by driving joint motors) to provide haptic feedback to the surgeon via the robotic arm 36. Here, haptic feedback help constrain or inhibit the surgeon from manually moving the end effector 40 and/or the tool 42 beyond predefined virtual boundaries associated with the surgical procedure (e.g., to maintain alignment of the workpiece 44 relative to the surgical site ST). One type of haptic feedback system and associated haptic objects that define virtual boundaries are described, for example, in U.S. Pat. No. 8,010,180, entitled "Haptic Guidance System and Method," the disclosure of which is hereby incorporated by reference in its entirety. In one example, the surgical system 30 is the RIO™ Robotic Arm Interactive Orthopedic System manufactured by MAKO Surgical Corp. of Fort Lauderdale, FL, USA.

While the representative example of the surgical system 30 illustrated in FIG. 1 employs the surgical robot 32 to facilitate positioning the tool 42 and workpiece 44 relative to the surgical site ST, the surgical system 30 may also and/or alternatively employ navigated hand-held tools, instruments, and the like which are tracked by the localizer 54 to facilitate navigated surgery (not shown, but generally known in the related art). The navigation system 48 can be utilized in connection with a number of different types of surgical systems 30, both robotically-controlled and/or hand-operated, for various navigated medical and surgical procedures.

In the representative example illustrated in FIG. 1, the localizer 54 is an optical localizer and includes a camera unit 72 with one or more optical sensors 74. The navigation system 48 employs the optical sensors 74 of the camera unit 72 to sense or otherwise monitor the position and/or orientation of each of the trackers 56 within the localizer coordinate system LCLZ based on the trackable features 58 observed within the field of view FV of the localizer 54. The trackers 56 each generally comprise a respective tracker body 76 which, as described in greater detail below, may define or otherwise support one or more trackable features 58 configured to be monitored by the localizer 54. In the representative example illustrated in FIGS. 1 and 8A-9C, the trackable features 58 are realized by four generically-depicted passive markers 78 which are shaped and arranged about the tracker body 76 in a predetermined manner that can be recognized and tracked by the optical position sensors 74 of the camera unit 72 of the localizer 54. In some examples, the localizer 54 or another part of the navigation system 48 may comprise an emitter module 80 configured to generate "pulses" of infrared or near-infrared light at a predetermined frequency which, when reflected back to the camera unit 72 by passive markers 78, facilitates monitoring the trackers 56 within the field of view FV of the localizer 54. As is described in greater detail below, the emitter module 80 is separate and distinct from the illumination assembly 60, which directs visible light toward the passive markers 78 to facilitate communicating the status condition SC and/or the system condition MC by reflecting visible light to the user.

While the representative example of the trackers 56 depicted in FIGS. 1 and 3A-4E employ trackable features 58 realized as passive markers 78, in some examples the trackers 56 could employ active markers (e.g., light emitting diodes "LEDs") which emit light (e.g., infrared or near-infrared light) that is sensed by the optical position sensors 74 of the camera unit 72. Examples of localizers 54, trackers 56, and navigation systems 48 are described in U.S. Pat. No. 9,008,757, entitled "Navigation System Including Optical and Non-Optical Sensors," the disclosure of which is hereby incorporated by reference in its entirety. As will be appreciated from the subsequent description below, other suitable tracking systems and methods not specifically described herein may be utilized in connection with the navigation system 48 (e.g., ultrasonic, electromagnetic, radio frequency, machine-vision, and the like).

Although the example of the navigation system 48 is illustrated throughout the drawings is based on "passive" trackers 56 and an optically-based localizer 54, the navigation system 48 may have other suitable configurations for monitoring trackers 56 which, as will be appreciated from the subsequent description below, may likewise be of various types and configurations. Thus, the navigation system 48 may comprise other types of localizers 54 and/or trackers 56 beyond those specifically described herein and illustrated throughout the drawings.

In some examples, the navigation system 48 and/or the localizer 54 are radio frequency (RF) based. For example, the navigation system 48 may comprise an RF transceiver coupled to the navigation controller 52 and/or to the control system 46 (e.g., to the arm controller 50). Here, the trackers 56 may comprise RF emitters or transponders, which may be passive or may be actively energized. The RF transceiver transmits an RF tracking signal, and the RF emitters respond with RF signals such that tracked states are communicated to (or interpreted by) the navigation controller 52. The RF signals may be of any suitable frequency. The RF transceiver may be positioned at any suitable location to track the objects using RF signals effectively. Furthermore, examples of RF-based navigation systems may have structural configurations that are different than the navigation system 48 illustrated throughout the drawings.

In some examples, the navigation system 48 and/or localizer 54 are electromagnetically (EM) based. For example, the navigation system 48 may comprise an EM transceiver coupled to the navigation controller 52 and/or to the control system 46 (e.g., to the arm controller 50). Here, the trackers 56 may comprise EM components attached thereto (e.g., various types of magnetic trackers, electromagnetic trackers, inductive trackers, and the like), which may be passive or may be actively energized. The EM transceiver generates an EM field, and the EM components respond with EM signals such that tracked states are communicated to (or interpreted by) the navigation controller 52. The navigation controller 52 may analyze the received EM signals to associate relative states thereto. Here too, examples of EM-based navigation systems may have structural configurations that are different than the navigation system 48 illustrated throughout the drawings.

In some examples, the navigation system 48 and/or the localizer 54 could be based on one or more other types of tracking systems. For example, an ultrasound-based tracking system coupled to the navigation controller 52 and/or to the control system 46 (e.g., to the arm controller 50) could be provided to facilitate acquiring ultrasound images of markers that define trackable features 58 such that tracked states TS are communicated to (or interpreted by) the navigation controller 52 based on the ultrasound images. By way of further example, a fluoroscopy-based imaging system (e.g., a C-arm) coupled to the navigation controller 52 and/or to the control system 46 (e.g., to the arm controller 50) could be provided to facilitate acquiring X-ray images of radio-opaque markers that define trackable features 58 such that tracked states TS are communicated to (or interpreted by) the navigation controller 52 based on the X-ray images. Furthermore, in some examples, a machine-vision tracking system (e.g., one or more charge-coupled devices) coupled to the navigation controller 52 and/or to the control system 46 (e.g., to the arm controller 50) could be provided to facilitate acquiring 2D and/or 3D machine-vision images of structural features that define trackable features 58 such that tracked states TS are communicated to (or interpreted by) the navigation controller 52 based on the machine-vision images. The ultrasound, X-ray, and/or machine-vision images may be 2D, 3D, or a combination thereof, and may be processed by the navigation controller 52 in near real-time to determine the tracked states TS.

Various types of tracking and/or imaging systems could define the localizer 54 and/or form a part of the navigation system 48 without departing from the scope of the present disclosure. Furthermore, the navigation system 48 and/or localizer 54 may have other suitable components or structure not specifically recited herein, and the various techniques, methods, and/or components described herein with respect to the optically-based navigation system 48 shown throughout the drawings may be implemented or provided for any of the other examples of the navigation system 48 described herein. For example, the navigation system 48 may utilize solely inertial tracking and/or combinations of different tracking techniques, sensors, and the like. Other configurations are contemplated.

Referring now to FIGS. 1-9C, as noted above, the navigation system 48 of the present disclosure employs the illumination assembly 60 to, among other things, direct light at one or more trackers 56 such that light reflected by a tracker 56 from the illumination assembly 60 is visible to the user to communicate the status condition SC of that tracker 56 determined by the navigation controller 52 (hereinafter, "controller 52") and/or to communicate the system condition MC of the surgical system 30 to the user. It will be appreciated that status conditions SC and/or system conditions MC could be defined in a number of different ways. In some configurations, the status condition SC and/or system condition MC could comprise respective normal conditions NC or error conditions EC, each of which could be defined in various ways. For example, a status condition SC of a particular tracker 56 could be defined as a normal condition NC when that tracker 56 is being actively and accurately monitored by the navigation system 48, and could be defined as an error condition when that tracker 56 is obstructed or otherwise inaccurately monitored. Other configurations are contemplated.

By way of further example, a system condition MC of the surgical system 30 could be defined as a normal condition NC when all trackers 56 are being actively and accurately monitored by the navigation system 48, and could be defined as an error condition when at least one tracker 56 is obstructed or otherwise inaccurately monitored. However, it will be appreciated that system conditions MC could relate to other aspects of the surgical system 30 itself and/or the workflow associated with a particular surgical procedure. Here, for example, the illumination assembly 60 could be used to direct light at one or more trackers 56 such that light reflected by a tracker 56 from the illumination assembly 60 is visible to the user to communicate changes in the system condition MC of the surgical system 30 to the user that are based on one or more of: a change a change in the operating mode of the robotic arm 36 (e.g., between autonomous and manual modes), a change in the relative position of a surgical tool relative to the patient's anatomy (e.g., approaching a boundary; virtual constraint; desired location, orientation, and/or depth; and the like), a change in the focus of a surgical procedure's workflow (e.g., cutting one bone as opposed to a different bone), a change in the utilization of multiple trackers 56 (e.g., one tracker 56 is visible to the navigation system 48 but is not utilized during a particular part of a surgical procedure), and the like. Other configurations are contemplated. Further examples of system conditions MC may include, without limitation: actual or expected collisions with the robotic arm 36 and/or navigation system 48; system errors such as tracking errors or robotic system errors, loss of accuracy or registration, and the like.

In some examples, trackers 56 may comprise a reflective feature, generically indicated at 82, that is operatively attached to the tracker body 76 in a predetermined arrangement relative to one or more trackable features 58 of the tracker 56. Here, the arrangement of the trackable features 58 and/or the reflective feature 82 relative to the tracker body 76 is known by the navigation system 48, and may be stored a non-transitory storage medium such as a memory device 84 disposed in communication with one or more processors 86 of the controller 52 (depicted schematically in FIG. 2). Various components of the surgical system 30 may employ separate memory devices, processors, circuits, and the like of various configurations and types, which may communicate with one another via wired and/or wireless communication (not shown in detail, but generally known in the related art).

The reflective feature 82 is separate from the one or more trackable features 58 and is configured to reflect visible light toward the user, as noted above. To this end, in some examples, the reflective feature 82 comprises a retroreflective material and the controller 52 is further configured to direct light at the reflective feature 82 (e.g., at coordinate associated with the location of the reflective feature 82 about the tracker body 76 based on the tracked states TS) such that light reflected by the reflective feature 82 from the illumination assembly 60 is visible to the user of the navigation system 48 to communicate the status condition SC of the tracker 56. However, other configurations are contemplated, and the reflective feature 82 could be realized in other ways without departing from the scope of the present disclosure. By way of non-limiting example, rather than comprising a retroreflective material, the reflective feature 82 could also be realized as a discrete portion of the tracker body 76 that is separate from, or is otherwise distinguishable by the localizer 54 from, the one or more trackable features 58 of the tracker 56 but is nevertheless configured to at least partially reflect visible light emitted by the illumination assembly 60 so as to be observable by the user to communicate the status condition SC or the system condition MC. Other configurations are contemplated.

As noted above, certain types of optically-based localizers 54 are configured to monitor trackers 56 with trackable features 58 that are realized as passive markers 78, whereby infrared or near-infrared light from the emitter module 80 is reflected by the passive markers 78 back to the optical position sensors 74 of the localizer 54. With these types of optically-based localizers 54 and trackers 56, light from the emitter module 80 that is reflected by the passive markers 78 is separate and distinguishable from light emitted by the illumination assembly 60 that is reflected by the reflective feature 82 based, among other things, on wavelength. As will be appreciated from the subsequent description below, in the illustrated examples, the illumination assembly 60 is not configured to direct light at the trackable features 58, and light emitted by the illumination assembly 60 does not facilitate monitoring the tracked states TS of the trackers 56 via the localizer 54.

The illumination assembly 60 may be utilized in connection with examples where the trackers 56 employ reflective features 82 comprising retroreflective material that is targeted by the illumination assembly 60, as well as examples where the trackers 56 are configured in other ways (e.g., without retroreflective materials, with "active marker" trackable features 58, and the like). Moreover, the navigation system 48 of the present disclosure is configured for use with a number of different types of trackers 56, including without limitation those which employ "active" trackable features 58 that are energized by a power source 88 coupled to the tracker 56 in order to be monitored by the localizer 54 (see FIG. 2; depicted schematically) and/or "passive" trackable features 58 that can be monitored by the localizer 54 without requiring a power source 88 to be coupled to the tracker 56 (e.g., realized with passive markers 78). Other configurations are contemplated.

Figure 2:
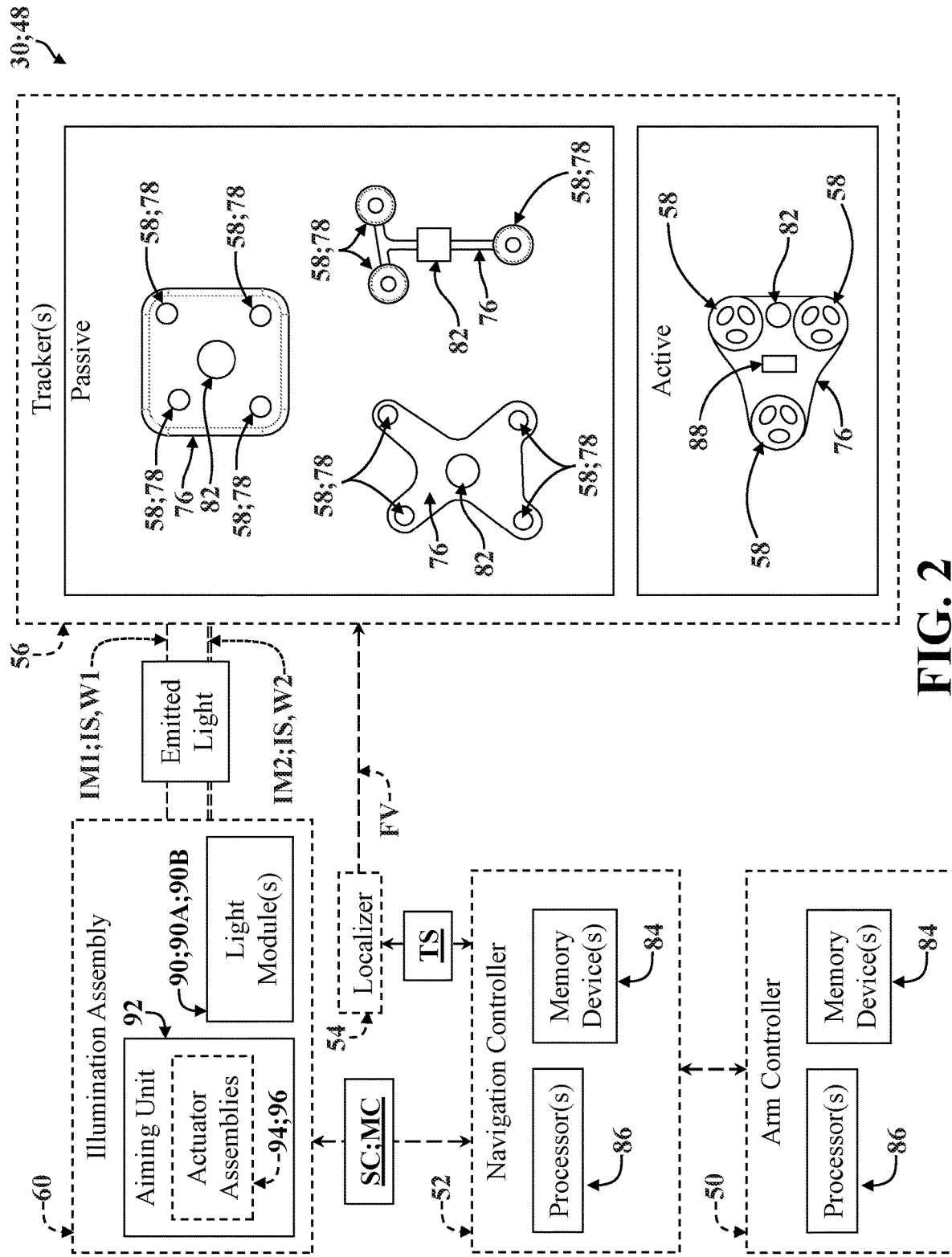
FIG. 2 is a schematic diagram of a controller in communication with the localizer and the illumination assembly of FIG. 1, shown with different types of trackers each having respective trackable features and reflective features according to examples of the present disclosure.

Referring now to FIG. 2, certain aspects of the surgical system 30 are depicted schematically. As noted above, the navigation system 48 employs the illumination assembly 60 to, among other things, direct light within the field of view FV. To this end, the illustrated examples of the illumination assembly 60 generally comprise a light module 90 and an aiming unit 92 that are disposed in communication with the controller 52, such as by wired or wireless communication. One or more sub-controllers or other electrical components (not shown) could also be employed by the illumination assembly 60 to facilitate operating the light module 90 and/or the aiming unit 92 (e.g., disposed in communication with the controller 52). Other configurations are contemplated. The light module 90 and the aiming unit 92 will each be described in greater detail below.

The light module 90 is generally operable between a first illumination mode IM1 to emit light, and a second illumination mode IM2 that is different from the first illumination mode IM1. As will be appreciated from the subsequent description below, the second illumination mode IM2 could be defined in various ways sufficient to be different from the first illumination mode IM1 without departing from the scope of the present disclosure. By way of non-limiting example, and as is described in greater detail below, the second illumination mode IM2 may comprise an illumination state IS that is defined by an absence of light emission by the light module 90. In this way, the user can readily appreciate the status condition SC of a particular tracker 56 based on whether or not light from the illumination assembly 60 is observable at that tracker 56.

The light module 90 itself could be operated between "on" to emit light in the first illumination mode IM1 and "off" to not emit light in the second illumination mode IM2. However, rather than operating the light module 90 "off" to define the second illumination mode IM2 for a particular tracker 56, the illumination assembly 60 could also be configured to direct light away from a particular tracker 56 via the aiming unit 92 to define the second illumination mode IM2, which may be implemented in examples where multiple trackers 56 are illuminated using a common illumination assembly 60 and/or a common light module 90, such as is described below in connection with the representative examples illustrated in FIGS. 8A-9C for example. Nevertheless, the user can readily differentiate the status condition SC of a particular tracker 56 based on whether or not observable light is reflected by the tracker 56 that is emitted via the illumination assembly 60.

In some examples, each illumination mode IM1, IM2 may comprise one or more illumination states IS which, in addition to differentiating the illumination modes IM1, IM2 from each other (e.g., to communicate changes in the status condition SC of a particular tracker 56 to the user) may also be utilized to simultaneously communicate system conditions MC to the user, as described in greater detail below. Like illumination modes IM1, IM2, illumination states IS may comprise or be based on, among other things, changes in the wavelength (e.g., color) and/or brightness of light, changes in whether light is being emitted at all (e.g., "on" or "off"), changes in patterns of light emission (e.g., light emitted in predetermined "blinking" sequences), and the like. Other configurations are contemplated.

As shown in FIG. 2, in some examples, the first illumination mode IM1 may comprise an illumination state IS defined by light emission at a first wavelength W1 (indicated by a single dashed line), and the second illumination mode IM2 may comprise an illumination state IS defined by light emission at a second wavelength W2 (indicated by a double dashed line) that is different from the first wavelength W1. In some embodiments, the first wavelength W1 is defined as light emission in a first color of visible light (e.g., green) and the second wavelength W2 is defined as light emission in a different second color of visible light (e.g., red). However, other colors, configurations, and the like are contemplated. As will be appreciated from the subsequent description below in connection with the examples illustrated in FIGS. 8A-9C, the second illumination mode IM2 could comprise various illumination states IS that can each nevertheless be differentiated from the first illumination mode IM1 (as well as from each other) in order to communicate status conditions SC and/or system conditions MC to the user.

In the representative examples illustrated herein, the light module 90 is depicted generically, and may comprise a number of different types, styles, configurations, and the like sufficient to emit light that can be directed within the field of view FV toward trackers 56. In some examples, the light module 90 may comprise a laser diode configured to emit light that can be directed toward the tracker 56 via the aiming unit 92, as described in greater detail below. However, other configurations are contemplated, and the light module 90 could be configured differently without departing from the scope of the present disclosure. By way of non-limiting example, the light module 90 may comprise one or more Light Emitting Diodes (e.g., single or multi-color LEDs) that cooperate with various optical components (e.g., various mirrors, lenses, light guides, and the like) to facilitate focusing, projecting, or otherwise directing light in predetermined ways within the field of view FV. In some examples, such as is depicted in FIGS. 7A-7D, the illumination assembly 60 may comprise first and second light modules 90A, 90B that can be operated independently and/or in coordinated ways by the controller 52 in to emit light at different wavelengths W1, W2 that, in some examples, may define different illumination modes IM1, IM2, different illumination states IS of one or more of the illumination modes IM1, IM2, and the like. Other configurations are contemplated.

With continued reference to FIG. 2, as noted above, the illumination assembly 60 employs the aiming unit 92 to facilitate directing light emitted by the light module 90 within the field of view FV. To this end, the examples of the aiming unit 92 described in greater detail below in connection with FIGS. 3-7D include a first actuator assembly 94 that is operable to direct light emitted by the light module 90 in a first direction D1 within the field of view FV, and a second actuator assembly 96 that is operable to direct light emitted by the light module 90 in a second direction D2 within the field of view FV, with the second direction D2 being different from the first direction D1. In the illustrated examples, the first direction D1 is substantially perpendicular to the second direction D2. However, other configurations are contemplated.

In the representative examples illustrated herein, the first actuator assembly 94 comprises a first rotary actuator 98 with a first shaft 100 supported by a first body 102 and arranged for movement about a first axis A1, and the second actuator assembly 96 comprises a second rotary actuator 104 with a second shaft 106 supported by a second body 108 and arranged for movement about a second axis A2 that is different from the first axis A1. However, and as will be appreciated by the subsequent description below, the aiming unit 92 may be of a number of different styles, types, and/or configurations sufficient to direct light within the field of view FV, and may comprise any suitable number of actuator assemblies of various types, configurations, and arrangements without departing from the scope of the present disclosure.

Figure 3:
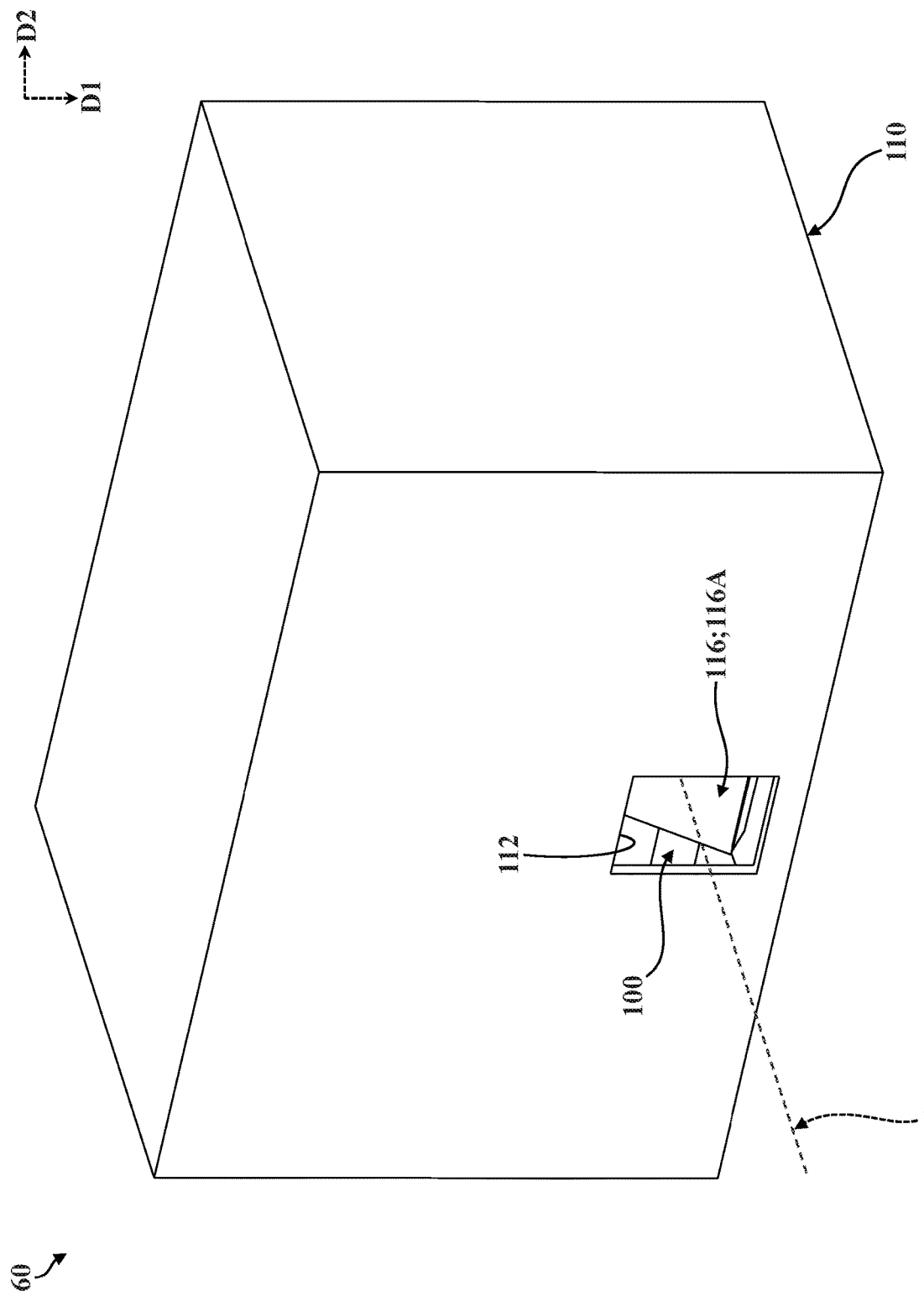
FIG. 3 is a perspective view of one example of the illumination assembly of the navigation system of FIG. 1, shown having a housing with an aperture through which light is directed.
Figure 4A:
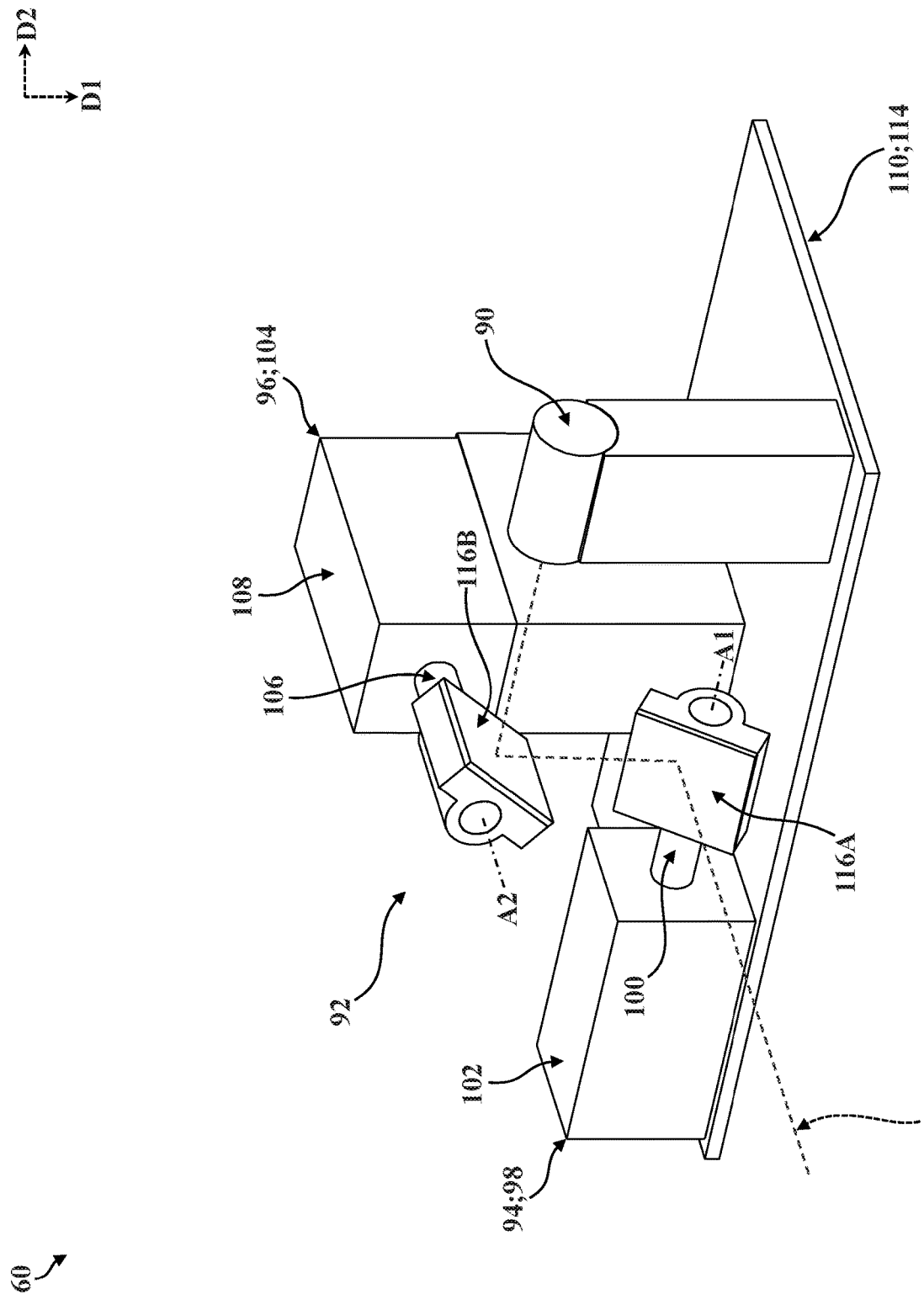
FIG. 4A is a partial perspective view of the illumination assembly of FIG. 3, shown having a light module emitting light at an aiming unit comprising first and second actuator assemblies having respective first and second mirrors arranged to direct light in a first direction.
Figure 4B:
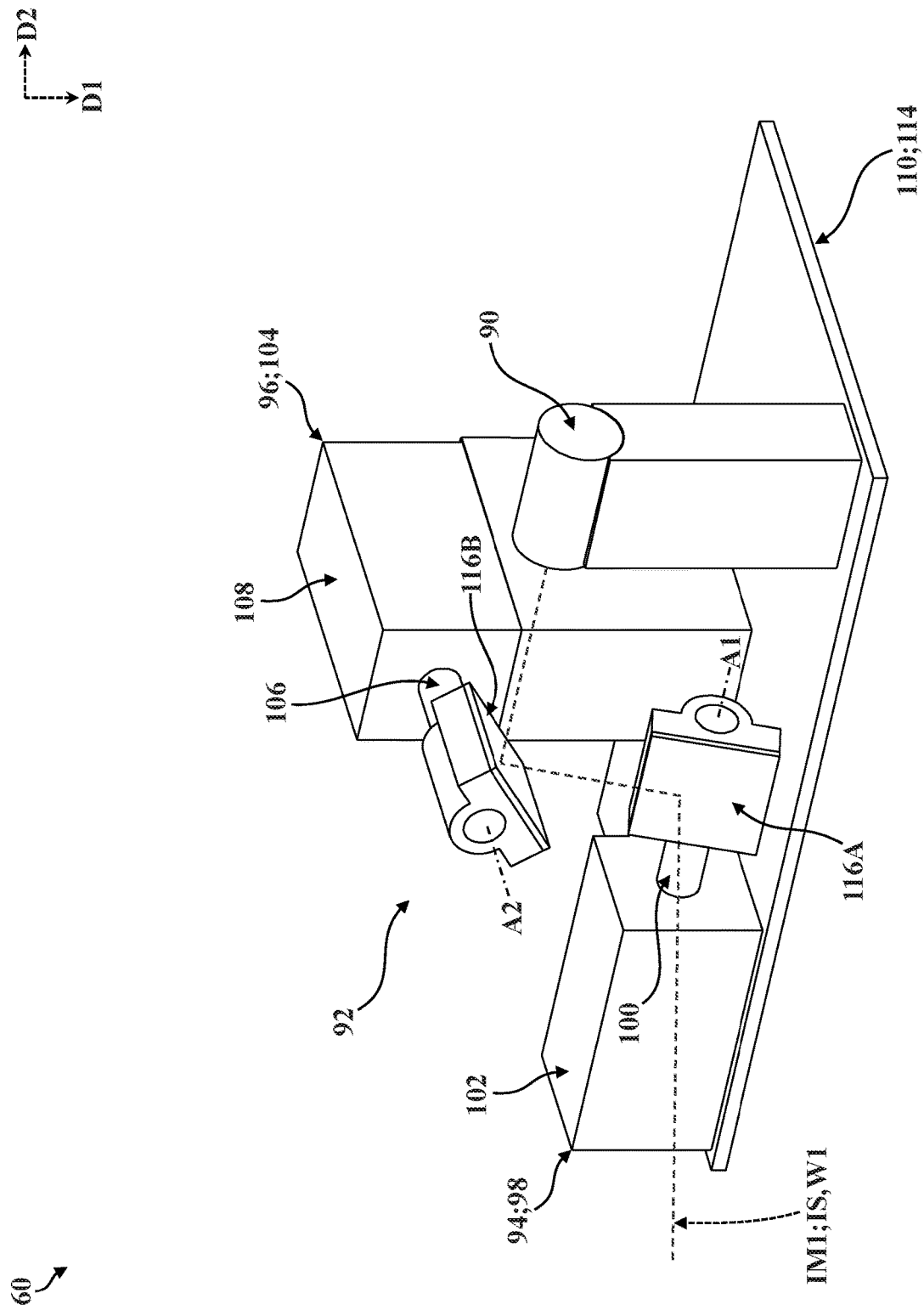
FIG. 4B is another partial perspective view of the illumination assembly of FIG. 4A, shown with the first and second mirrors of the respective first and second actuator assemblies arranged to direct light in a second direction.

Referring now to FIGS. 3-4B, the illustrated example of the illumination assembly 60 comprises a housing 110 defining a window 112 through which light emitted by the light module 90 can pass. The housing 110 also defines a mount 114 that supports various components of the illumination assembly 60 attached thereto (attachment not shown in detail). In this example, the aiming unit 92 also comprises a mirror, generally indicated at 116, that is operatively attached to the first shaft 100 of the first rotary actuator 98 for movement about the first axis A1 relative to the light module 90 to direct light emitted by the light module 90 in the first direction D1 within the field of view FV. More specifically, in this example, the mirror 116 may be further defined as a first mirror 116A, and the aiming unit 92 also comprises a second mirror 116B that is operatively attached to the second shaft 106 of the second rotary actuator 104 for movement about the second axis A2 relative to the light module 90 to direct light emitted by the light module 90 in the second direction D2 within the field of view FV. The second mirror 116B is arranged between the first mirror 116A and the light module 90 such that light emitted by the light module 90 is reflected from the second mirror 116B to the first mirror 116A before passing out of the window 112.

As shown in FIGS. 4A-4B, in this example of the illumination assembly 60, the light module 90 is secured to the mount 114 of the housing 110 and emits light that is directed at the second mirror 116B of the second actuator assembly 96 which, when moved about the second axis A2 via the second rotary actuator 104, effects movement of the light in the second direction D2. Here, light (e.g., light moving in the second direction D2) is reflected by the second mirror 116B to the first mirror 116A of the first actuator assembly 94 which, when moved about the first axis A1 via the first rotary actuator 98, effects (further) movement of the light in the first direction D1. By coordinating operation of the first and second actuator assemblies 94, 96 of the aiming unit 92, the controller 52 is able to quickly and efficiently direct light emitted by the light module 90 in the first and second directions D1, D2 (compare FIGS. 4A and 4B) within the field of view FV to facilitate communicating the status condition SC of the tracker 56, as noted above.

In some examples, the first and second actuator assemblies 94, 96 may form part of a "mirror galvanometer," a "laser projector," or a "scanning laser" that defines the illumination assembly 60 and allows the controller 52 to facilitate directing light to specific coordinates, locations, and the like within the field of view FV with a high degree of precision, accuracy, and speed. However, other configurations are contemplated, and the first and second actuator assemblies 94, 96 (as well as the light module 90) could be of a number of different styles, types, configurations, and the like configured to direct light within the field of view FV without departing from the scope of the present disclosure.

Figure 5A:
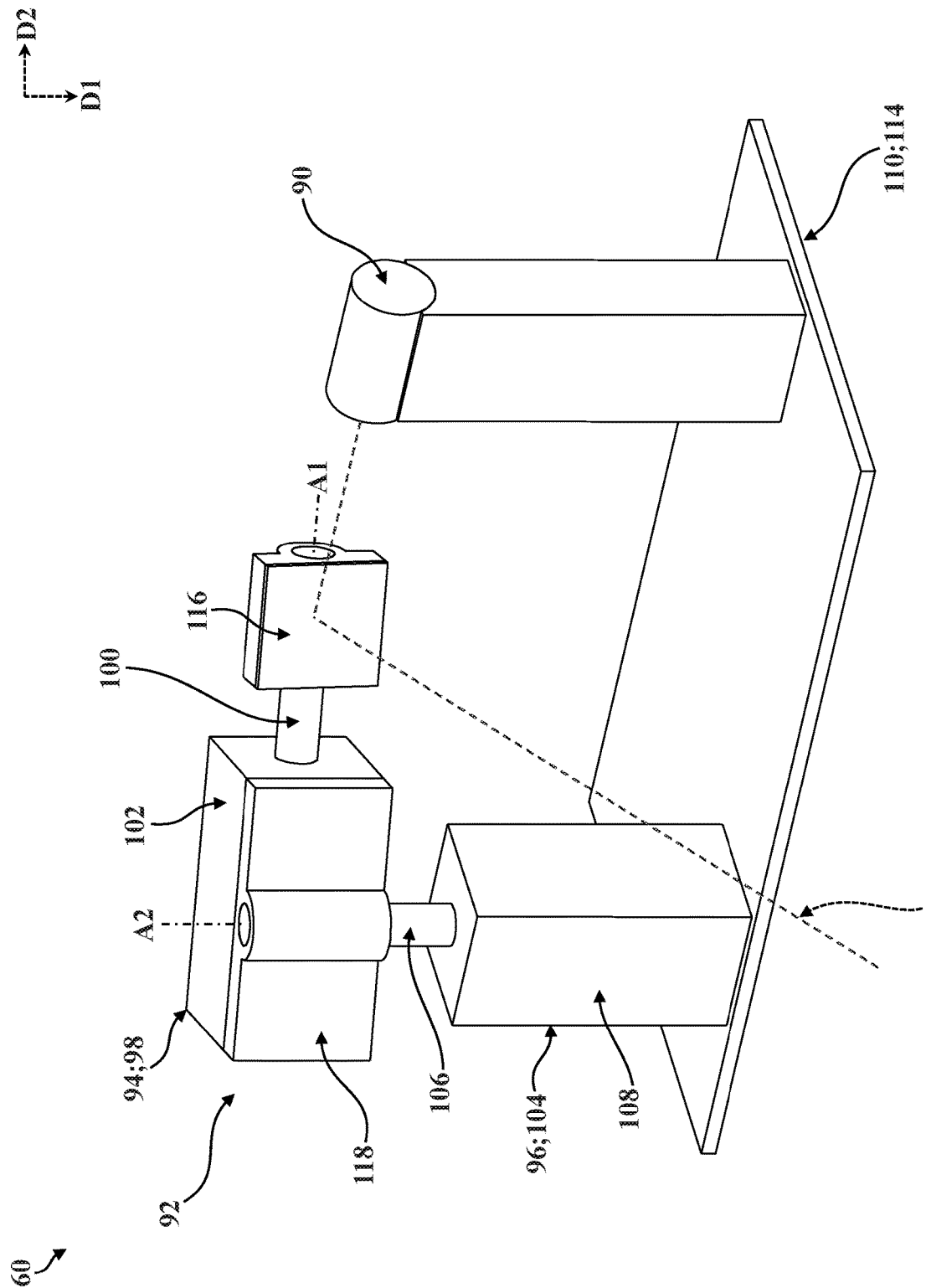
FIG. 5A is a partial perspective view of another example of the illumination assembly of the navigation system of FIG. 1, shown having a light module emitting light at an aiming unit comprising a first actuator assembly with a mirror supported by a second actuator assembly, with the mirror arranged to direct light in a first direction.
Figure 5B:
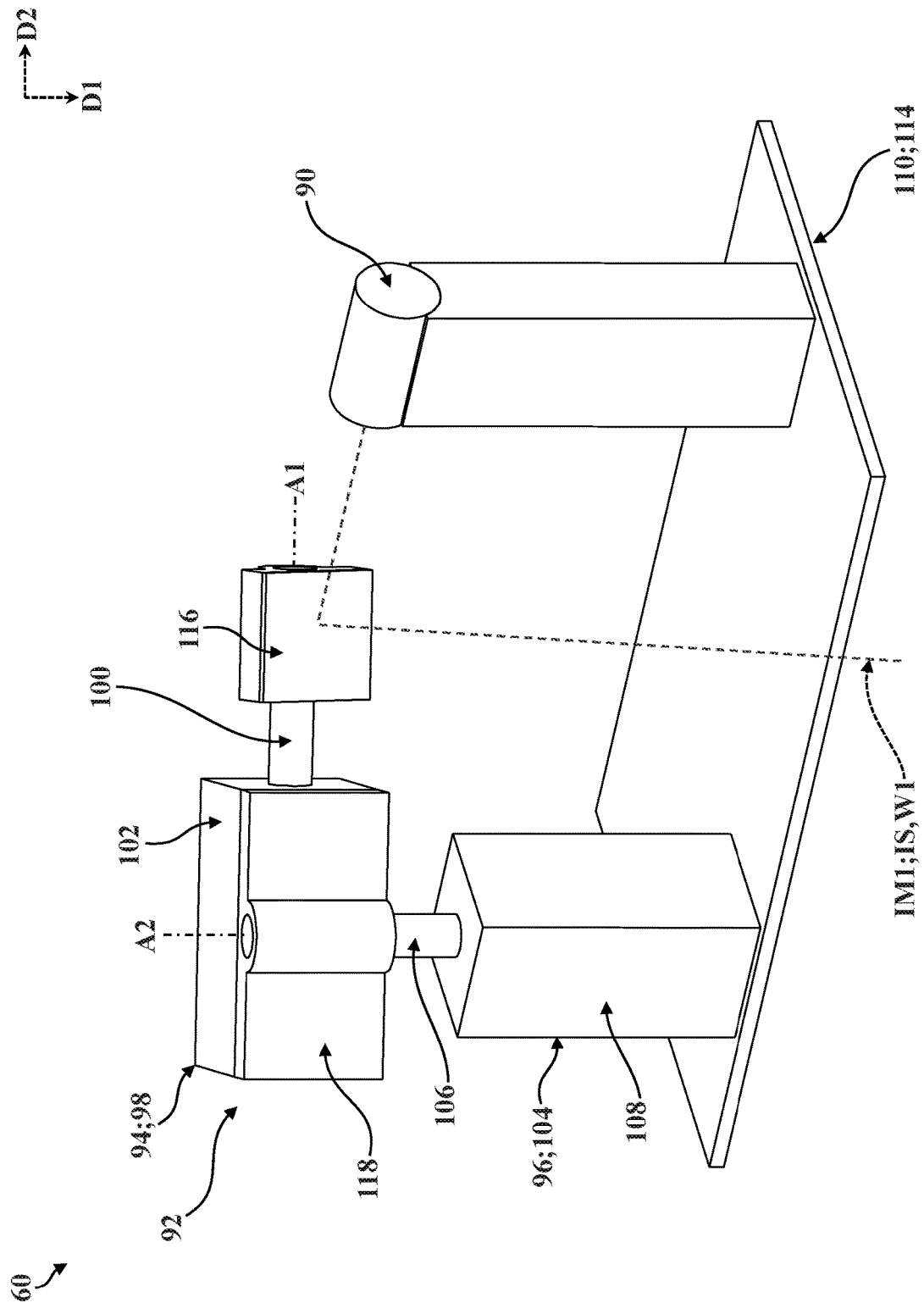
FIG. 5B is another partial perspective view of the illumination assembly of FIG. 5A, shown with the mirror arranged to direct light in a second direction.
Figure 6A:
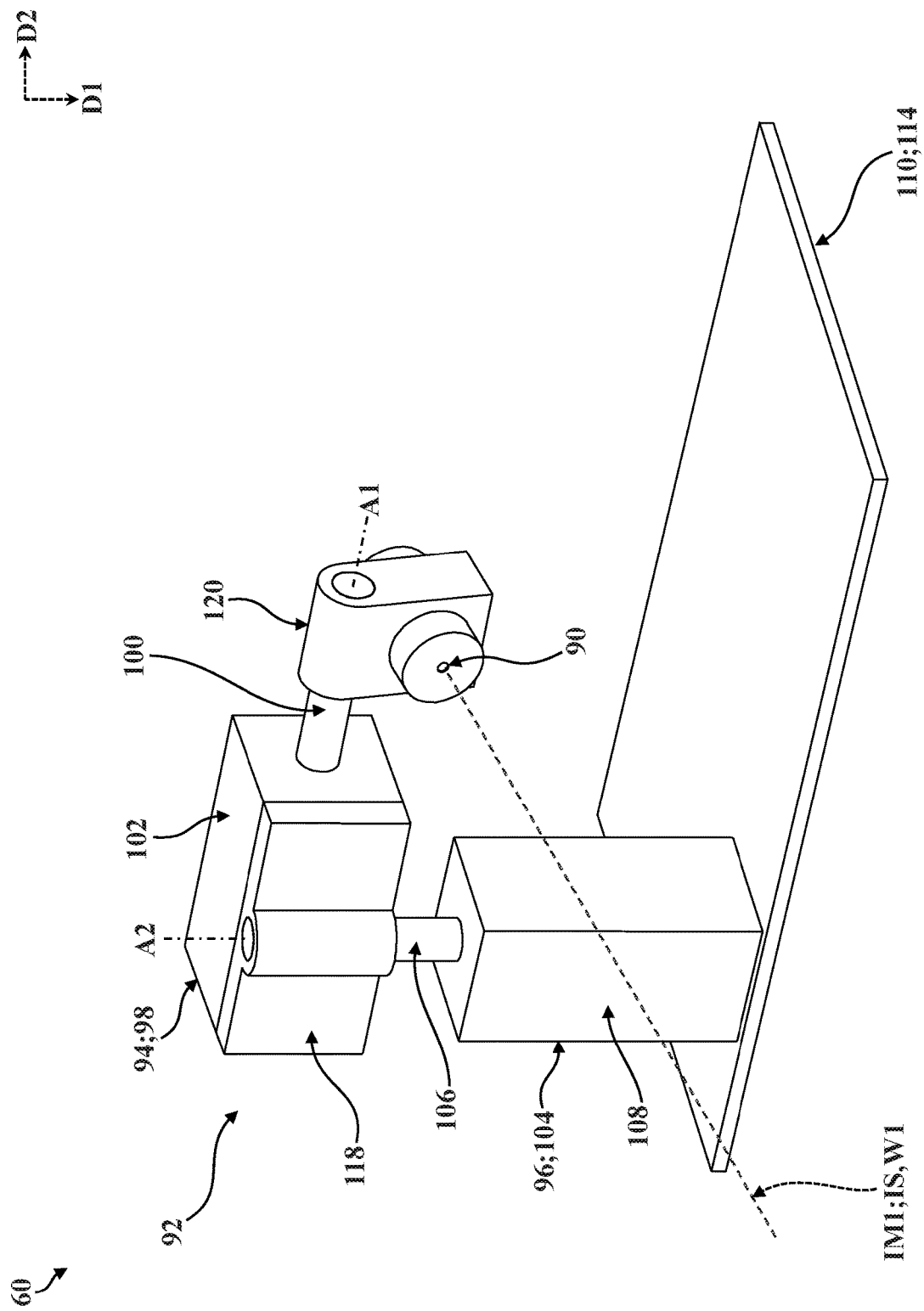
FIG. 6A is a partial perspective view of another example of the illumination assembly of the navigation system of FIG. 1, shown having an aiming unit comprising first and second actuator assemblies, with the first actuator assembly shown supporting a light module emitting light, and with the aiming unit arranged to direct light emitted by the light module in a first direction.
Figure 6B:
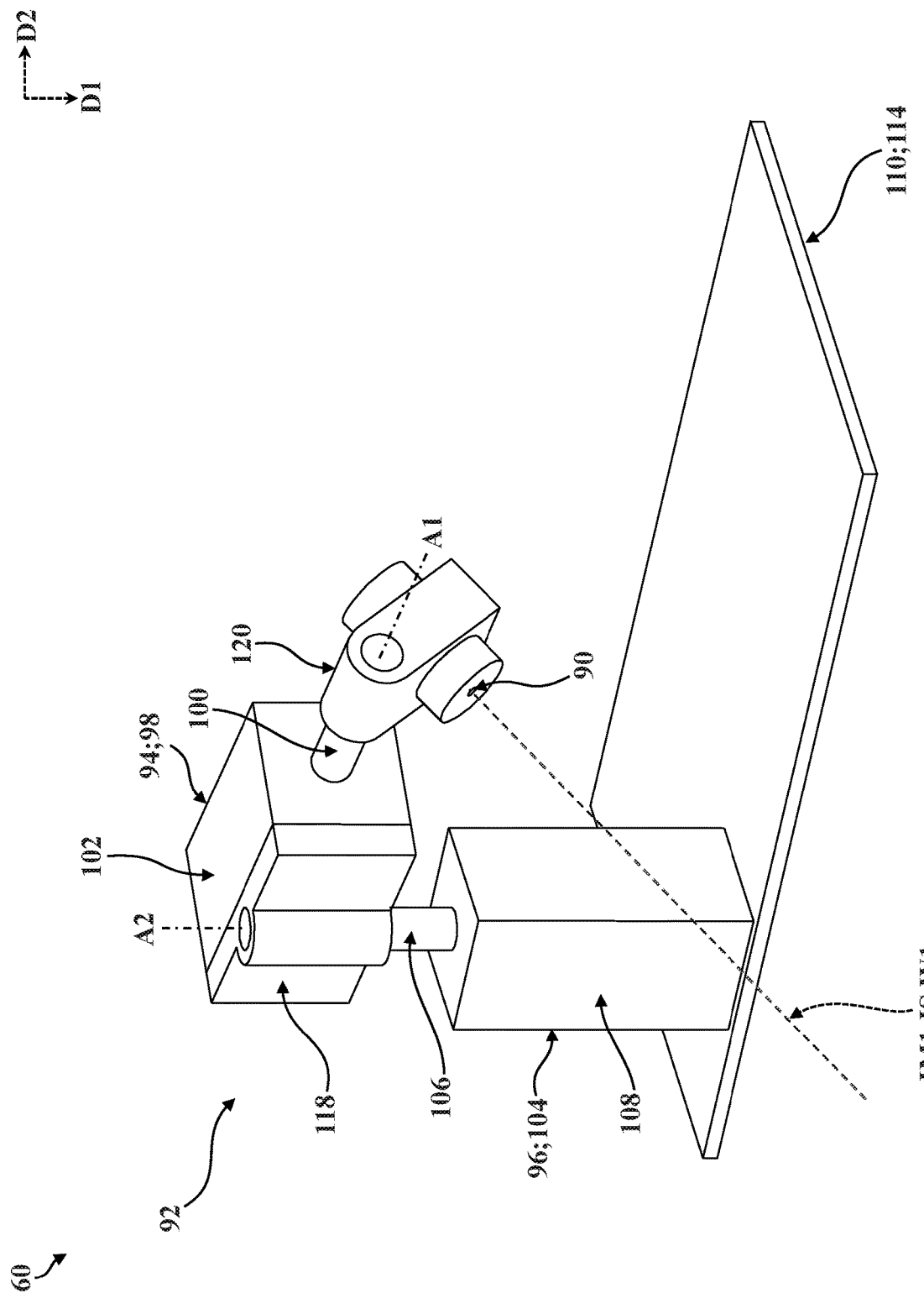
FIG. 6B is another partial perspective view of the illumination assembly of FIG. 6A, shown with the aiming unit arranged to direct light emitted by the light module in a second direction.
Figure 7A:
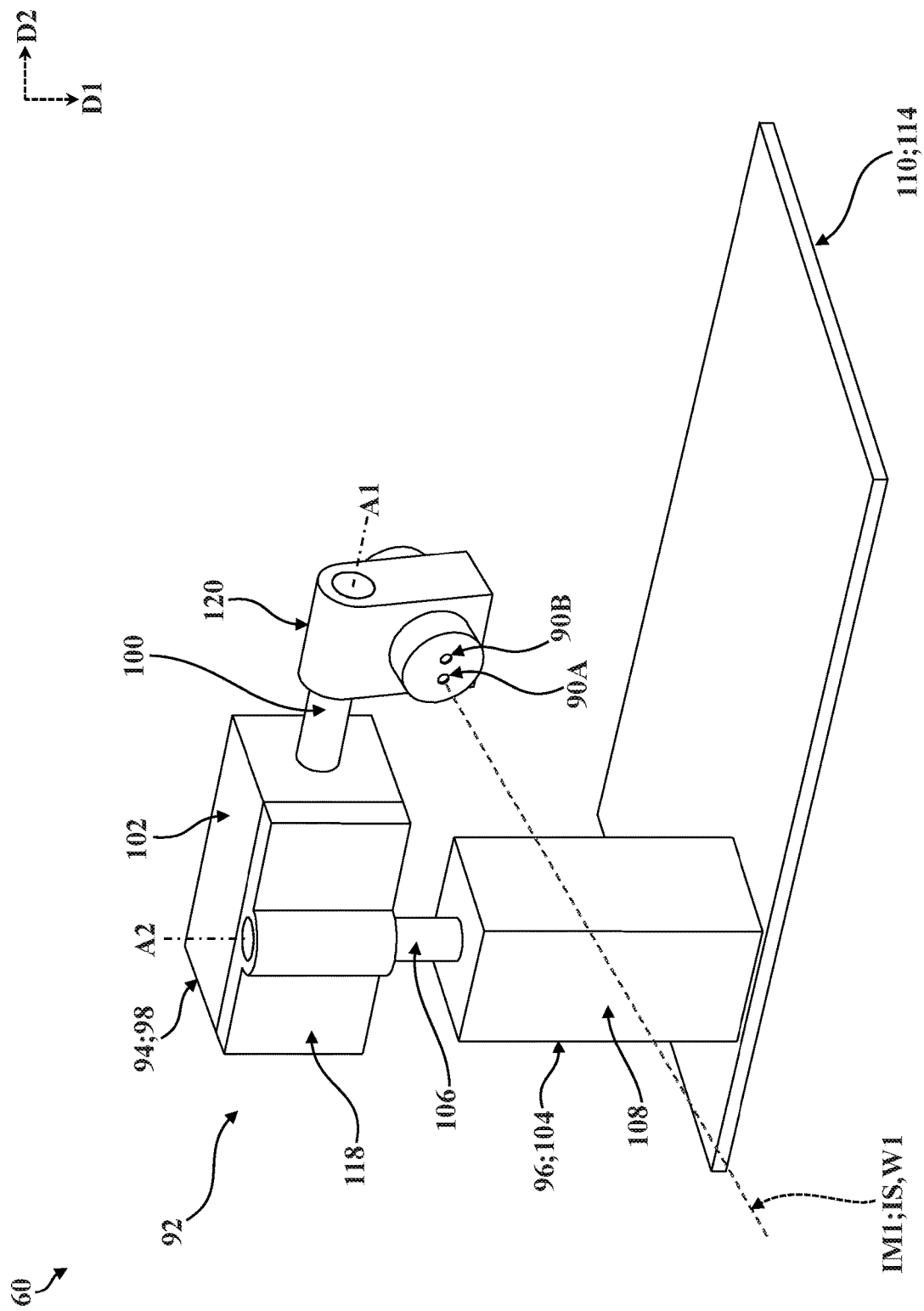
FIG. 7A is a partial perspective view of another example of the illumination assembly of the navigation system of FIG. 1, shown having an aiming unit comprising first and second actuator assemblies, with the first actuator assembly shown supporting first and second light modules with the first light module emitting light, and with the aiming unit arranged to direct light emitted by the first light module in a first direction.
Figure 7B:
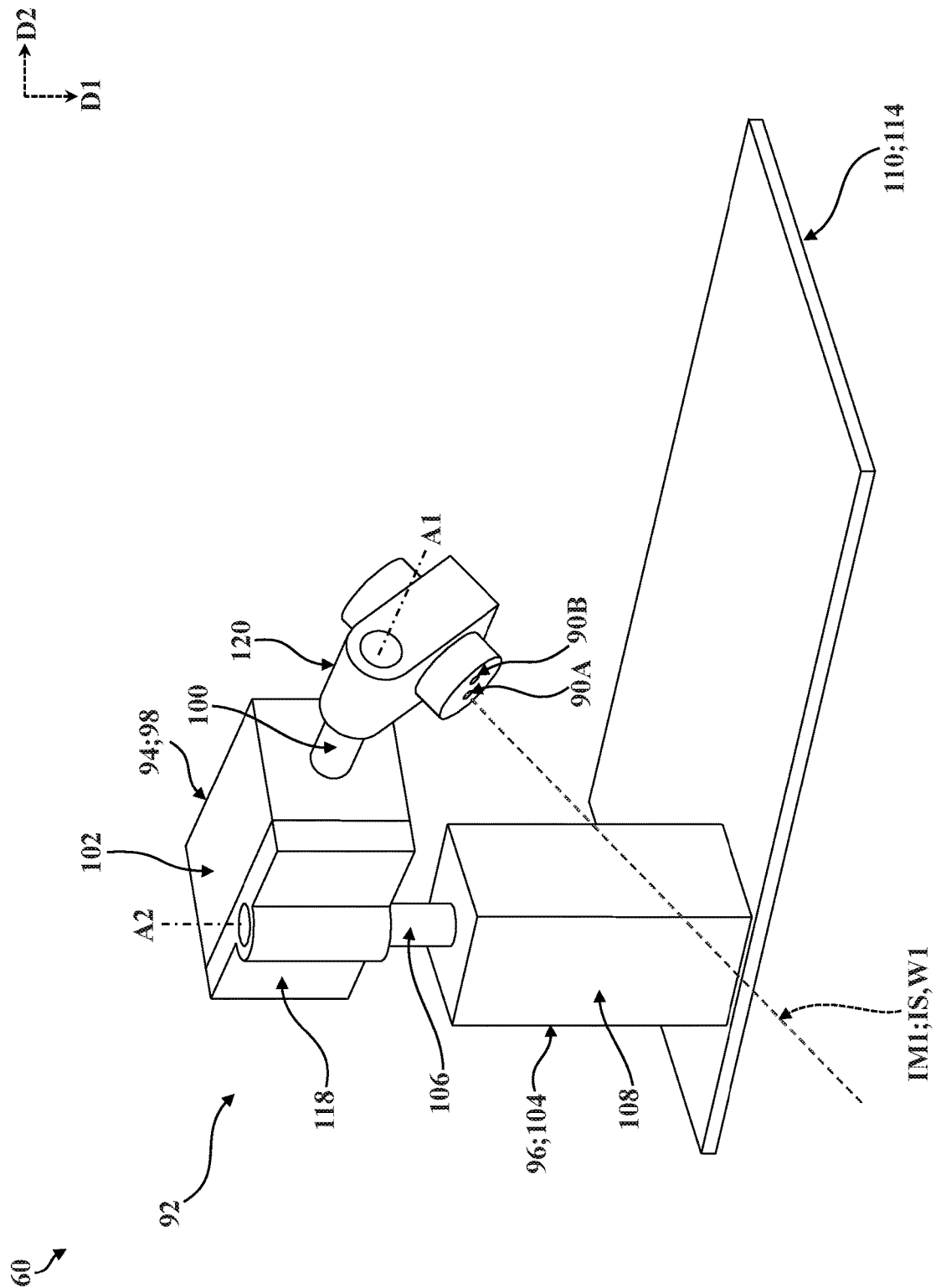
FIG. 7B is another partial perspective view of the illumination assembly of FIG. 7A, shown with the aiming unit arranged to direct light emitted by the first light module in a second direction.
Figure 7C:
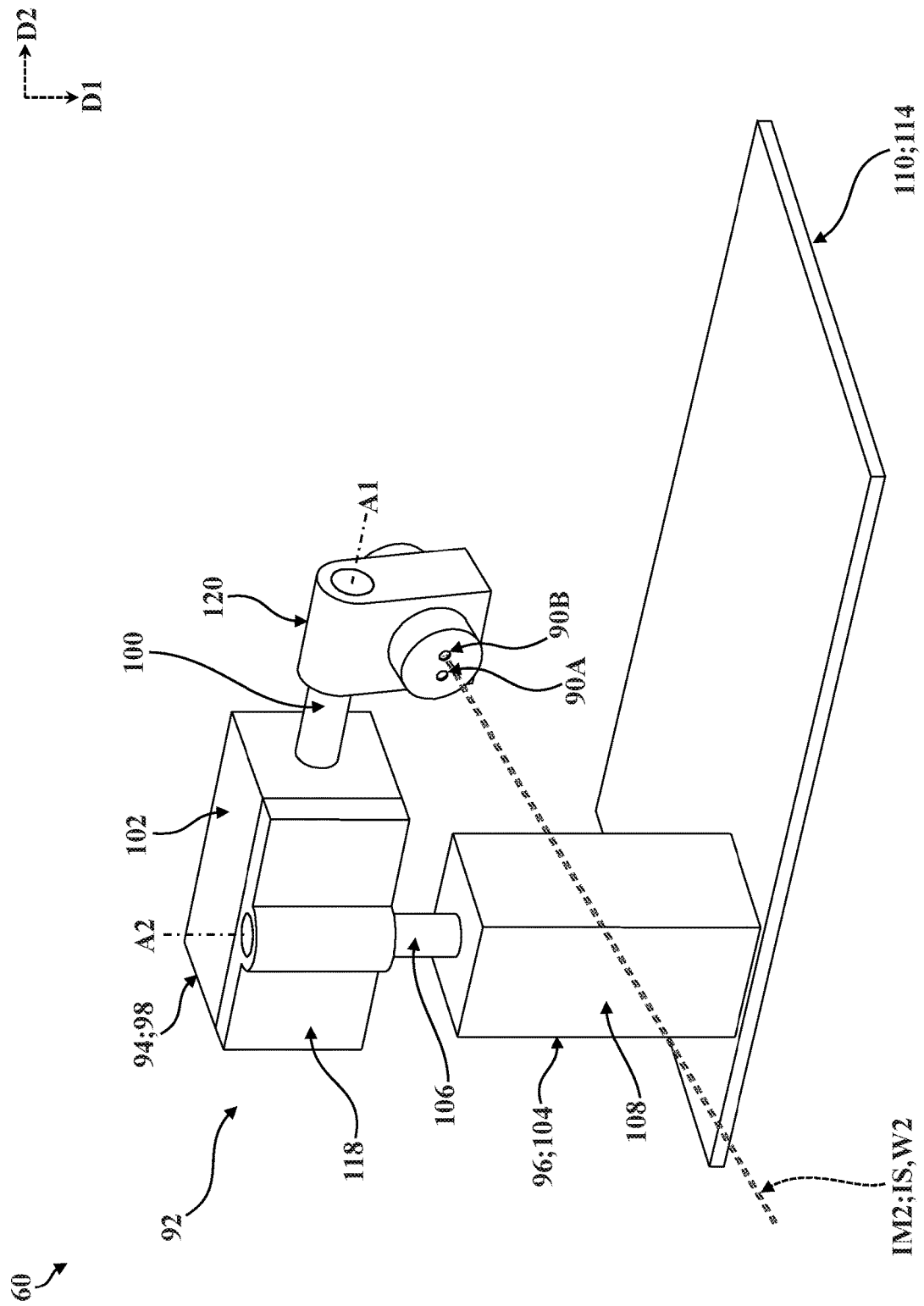
FIG. 7C is another partial perspective view of the illumination assembly of FIG. 7B, shown with the aiming unit arranged to direct light emitted by the second light module in the first direction.
Figure 7D:
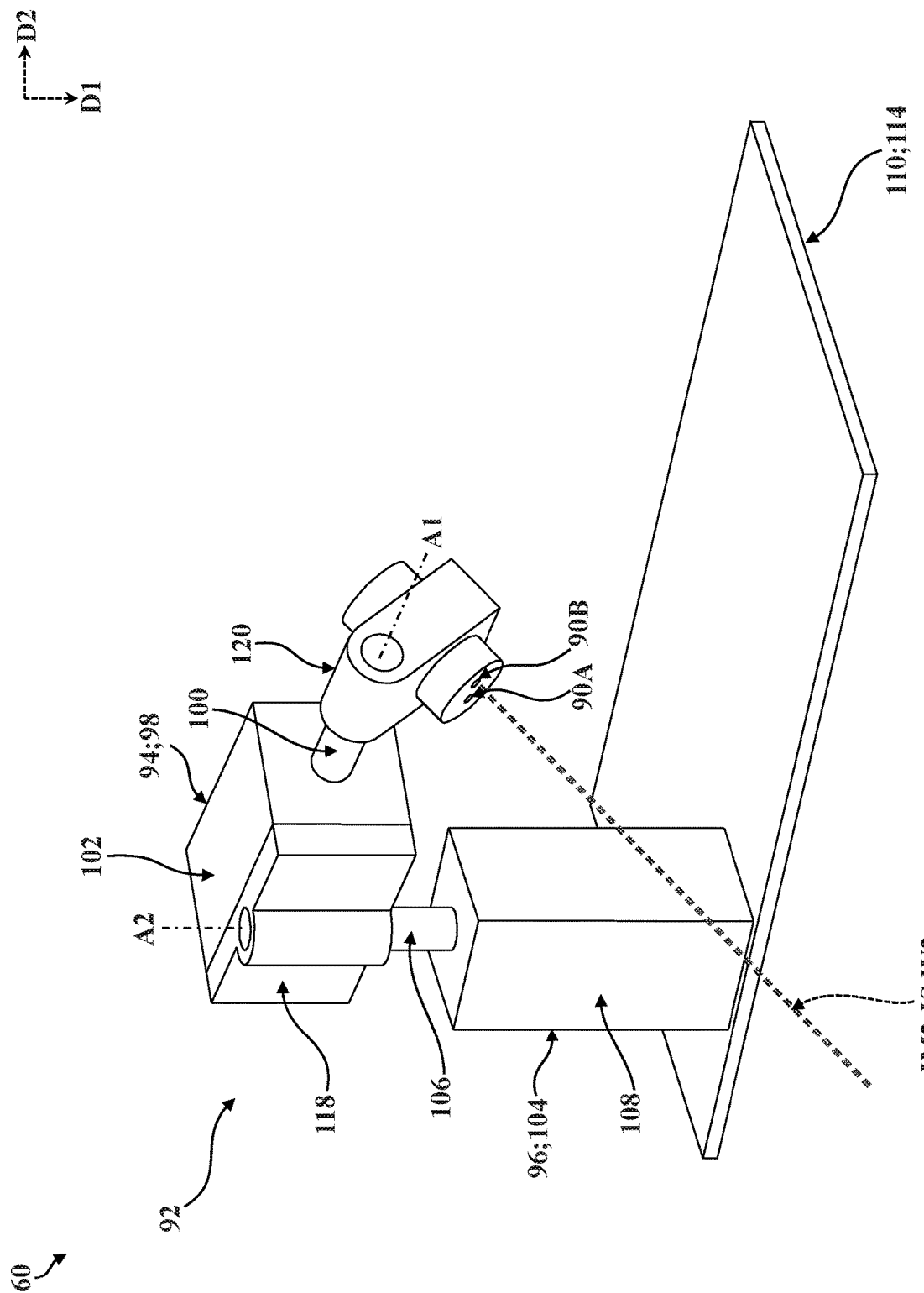
FIG. 7D is another partial perspective view of the illumination assembly of FIG. 7C, shown with the aiming unit arranged to direct light emitted by the second light module in the second direction.

Referring now to FIGS. 5A-5B, in this example of the illumination assembly, only a single mirror 116 is utilized and the aiming unit 92 further comprises a carrier 118 that is coupled to the second shaft 106 of the second rotary actuator 104 for concurrent movement about the second axis A2. Here, the second body 108 of the second rotary actuator 104 is secured to the mount 114, and the first actuator assembly 94 is coupled to the carrier 118 for concurrent movement about the second axis A2 with the second shaft 106. The first actuator assembly 94 supports the mirror 116 coupled to the first shaft 100 for movement about the first axis A1. In this example, the light module 90 is likewise secured to the mount 114 of the housing 110 and emits light that is directed at the mirror 116, but the mirror 116 is effectively arranged for movement relative to the light module 90 in both the first and second directions D1, D2 based on movement about the first and second axes A1, A2, respectively. Here too in this example, by coordinating operation of the first and second actuator assemblies 94, 96 of the aiming unit 92, the controller 52 is able to quickly and efficiently direct light emitted by the light module 90 in the first and second directions D1, D2 (compare FIGS. 5A and 5B) within the field of view FV to facilitate communicating the status condition SC of the tracker 56, as noted above.

While the light module 90 is spaced from one or more of the first actuator assembly 94 and the second actuator assembly 96 in the examples of the illumination assembly 60 depicted in FIGS. 4A-5B, other configurations are contemplated. For example, and with reference to the example illustrated in FIGS. 6A-6B, the light module 90 itself may be supported by a coupling 120 secured to the first shaft 100 of the first rotary actuator 98 for concurrent movement about the first axis A1. Here, like the example described above in connection with FIGS. 5A-5B, the first body 102 of the first rotary actuator 98 is coupled to the carrier 118 which, in turn, is coupled to the second shaft 106 of the second rotary actuator 104 for concurrent movement about the second axis A2. With this configuration, the aiming unit 92 moves the light module 90 via operation of the first and second actuator assemblies 94, 96 to effect movement of light emitted by the light module 90 in the first and second directions D1, D2 (compare FIGS. 6A and 6B) within the field of view FV to facilitate communicating the status condition SC of the tracker 56, as noted above.

Referring now to FIGS. 7A-7D, as noted above, this example of the illumination assembly 60 comprises first and second light modules 90A, 90B which can be independently operated by the controller 52. Here, like the example described above in connection with FIGS. 6A-6B, the illumination assembly 60 employs the coupling 120 to support the first and second light modules 90A, 90B to the first shaft 100 of the first rotary actuator 98 for concurrent movement about the first axis A1. Here too, the first body 102 of the first rotary actuator 98 is coupled to the carrier 118 which, in turn, is coupled to the second shaft 106 of the second rotary actuator 104 for concurrent movement about the second axis A2. With this configuration, the aiming unit 92 operated by the controller 52 moves the first and second light modules 90A, 90B via the first and second actuator assemblies 94, 96 to effect movement of light emitted by first and second light modules 90A, 90B in the first and second directions D1, D2 (compare FIGS. 7A-7D) within the field of view FV to facilitate communicating the status condition SC of the tracker 56, as noted above.

Figure 8A:
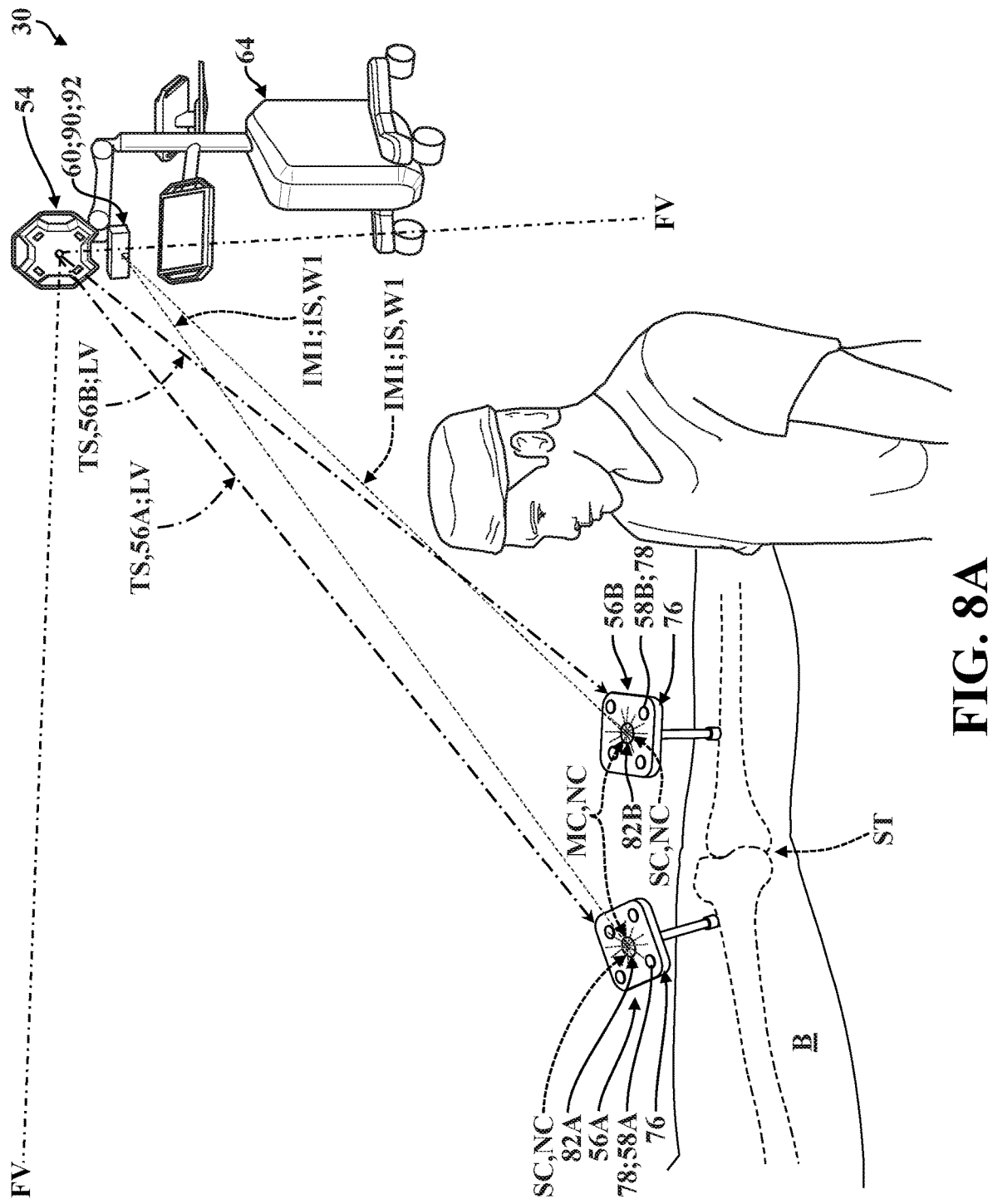
FIG. 8A is a partial perspective view of the navigation system of FIG. 1, shown with first and second trackers coupled to respective portions of the patient's body adjacent to the surgical site, and shown with an illumination assembly operatively attached to a localizer and directing light at each of the first and second trackers to communicate a normal condition for each of the first and second trackers.

Referring now to FIG. 8A, an example of the surgical system 30 with a navigation system 48 according to the present disclosure is shown with a patient undergoing a surgical procedure. Here, the surgical site ST is defined by the patient's right knee joint, and first and second patient trackers 56A, 56B are attached to adjacent bones of the patient's body B (e.g., the femur and the tibia) and are arranged within the field of view FV of the localizer 54. The user (e.g., a surgeon) is able to readily observe the first and second patient trackers 56A, 56B adjacent to the surgical site ST which, for the purposes of clarity and consistency in the subsequent description below, comprise respective first and second trackable features 58A, 58B as well as respective first and second reflective features 82A, 82B. In this example, the illumination assembly 60 is operatively attached to the localizer 54 (e.g., to a portion of the mobile cart 64). Accordingly, both the light module 90 and the aiming unit 92 are also operatively attached to the localizer 54 in this example. This arrangement allows the controller 52 to direct light emitted by the illumination assembly 60 within the field of view FV of the localizer 54 because the position and orientation of the illumination assembly 60 is "fixed" relative to the position and orientation of the localizer 54. However, and as described in greater detail below in connection with FIGS. 9A-9C, the illumination assembly 60 could be spaced from the localizer 54 in some examples.

In FIG. 8A, the localizer 54 has line-of-sight visibility LV (indicated by dash-dot lines) with each of the first and second patient trackers 56A, 56B. Based on visibility between the localizer 54 and the first and second trackable features 58A, 58B of the respective first and second patient trackers 56A, 56B illustrated in FIG. 8A, the controller 52 determines that the status conditions SC of each of the first and second patient trackers 56A, 56B are normal conditions NC. Put differently, the status conditions SC are normal conditions NC because the localizer 54 has an unobstructed view of the first and second trackable features 58A, 58B within the field of view FV and is thus able to accurately monitor tracked states TS of the first and second patient trackers 56A, 56B. However, the controller 52 could determine that the status conditions SC of the first and second patient trackers 56A, 56B are normal conditions NC in other ways without departing from the scope of the present disclosure. By way of non-limiting example, for non-optical type localizers 54 (e.g., electromagnetic RM, radio frequency RF, and the like), signal strength associated with tracked states TS may be utilized to determine status conditions SC. Other configurations are contemplated.

With continued reference to FIG. 8A, because each of the trackers 56 monitored by the localizer 54 within the field of view FV are determined to be in normal conditions NC, the controller 52 operates the illumination assembly 60 in the first illumination mode IM1 to direct light at both the first patient tracker 56A and the second patient tracker 56B in order to communicate the normal conditions NC to the user. Thus, light reflected by the first and second reflective features 82A, 82B can be readily observed by the user to communicate the status conditions SC (here, normal conditions NC) of each of the first and second patient trackers 56A, 56B. As will be appreciated from the subsequent description below, a change from the representative scenario illustrated in FIG. 8A may represent a change in the status condition SC of one or more trackers 56 from the normal condition NC (e.g., to an error condition EC).

Here too in FIG. 8A, the controller 52 determines that the system condition MC of the navigation system 48 is likewise in a normal condition NC, which in this example may be communicated to the user based on light being reflected at the same wavelength W1 by each of the first and second patient trackers 56A, 56B. As will be appreciated from the subsequent description below, a change from the representative scenario illustrated in FIG. 8A may also represent a change in the system condition MC of the navigation system 48 and/or the surgical system 30.

In some examples, the controller 52 is configured to control the illumination assembly 60 to scan light sequentially between the first and second patient trackers 56A, 56B such that the user observes uninterrupted "simultaneous illumination" of the first and second reflective features 82A, 82B (e.g., such as by driving the aiming unit 92 at high speed). With this configuration, a single light module 90 can be utilized to direct light at multiple trackers 56. However, as noted above, it is contemplated that multiple light modules 90 and/or illumination assemblies 60 could be utilized in certain examples without departing from the scope of the present disclosure.

Figure 8B:
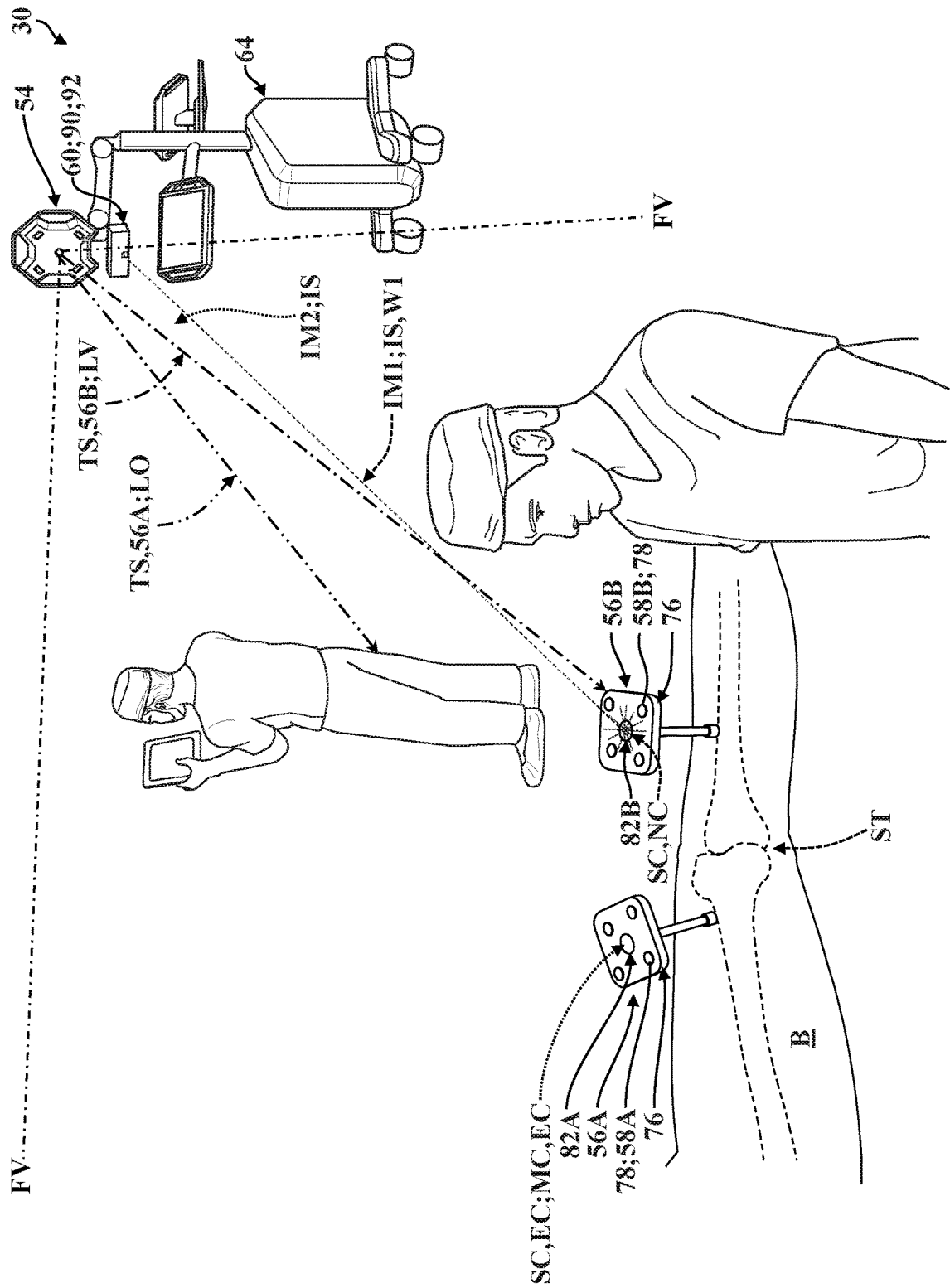
FIG. 8B is another partial perspective view of the navigation system of FIG. 8A, shown with a caregiver interrupting line-of-sight between the localizer and the first tracker, with the illumination assembly having interrupted directing light at the first tracker to communicate a tracker error condition to a user, and with the illumination assembly directing light at the second tracker in a first illumination mode to communicate the normal condition for the second tracker.

Continuing now to FIG. 8B from FIG. 8A, a caregiver is shown arranged between the localizer 54 and the first patient tracker 56A. Here, while the localizer 54 still has line-of-sight visibility LV (indicated by a dash-dot line) with the second trackable feature 58B of the second patient tracker 56B, there is a line-of-sight obstruction LO (indicated by a dash-dot-dot line) with the first trackable feature 58A of the first patient tracker 56A caused by the caregiver. Accordingly, the controller 52 determines that the status condition SC of the second patient tracker 56B is the normal condition NC based on visibility of the second trackable feature 58B, and determines that the status condition SC of the first patient tracker 56A is an error condition EC based on obstruction of the first trackable feature 58A. Here, the controller 52 operates the illumination assembly 60 to direct light at the second reflective feature 82B in order to communicate the normal condition NC of the second patient tracker 56B, but does not direct light at the first reflective feature 82A in order to communicate the error condition EC of the first patient tracker 56A.

In FIG. 8B, the absence of light emitted by the illumination assembly 60 toward the first patient tracker 56A in the second illumination mode IM2 is illustrated by a dotted arrow pointing to empty space (compare FIG. 8B with FIG. 8A), and the corresponding absence of light reflected by the first patient tracker 56A to communicate the status condition SC is illustrated by a dotted arrow pointing to the first reflective feature 82A.

In this example, for the second patient tracker 56B, the controller 52 operates the illumination assembly 60 in the first illumination mode IM1 when orientating the aiming unit 92 to direct light at the second reflective feature 82B in order to facilitate communicating the normal condition NC of the second patient tracker 56B to the user. However, for the first patient tracker 56A, the controller 52 operates the illumination assembly 60 in the second illumination mode IM2 (defined here as an absence of light emission) when orientating the aiming unit 92 in a way that would otherwise direct light at the first reflective feature 82A. Here, because the aiming unit 92 can "scan" light sequentially between the first and second patient trackers 56A, 56B, the controller 52 may be configured to coordinate operation of the aiming unit 92 and the light module 90 such that the light module 90 operates "on" in the first illumination mode IM1 when orientated at the second patient tracker 56B and "off" in the second illumination mode IM2 when orientated at the first patient tracker 56A. However, the controller 52 could also be configured to maintain orientation of the aiming unit 92 toward the second reflective feature 82B of the second patient tracker 56B while operating the light module 90 as "on" in the first illumination mode IM1 without directing any light toward the first reflective feature 82A of the first patient tracker 56A. Nevertheless, the configuration illustrated in FIG. 8B communicates the status conditions SC of the first and second patient trackers 56A, 56B to the user based on the presence or absence of light directed at the respective first and second reflective features 82A, 82B. Put differently, the user can readily discern changes in status conditions SC based on corresponding changes in the illumination of trackers 56 via the illumination assembly 60, such as for example the first patient tracker 56A changing from the normal condition NC as depicted in FIG. 8A to the error condition EC as depicted in FIG. 8B.

Comparing FIG. 8B with FIG. 8A demonstrates how the navigation system 48 can be utilized to communicate status conditions SC of individual trackers 56. Because the second patient tracker 56B is reflecting light emitted by the illumination assembly 60 at the first wavelength W1 (indicated by a single dashed line), but the first patient tracker 56A is not reflecting any light and was previously (compare FIG. 8B to FIG. 8A), the user can readily appreciate that the status condition SC of the second patient tracker 56B is the normal condition NC by observing light reflected by the second reflective feature 82B, and also that the status condition SC of the first patient tracker 56A has changed to the error condition EC by observing the absence of light reflected by the first reflected feature 82A.

While not depicted in connection with the representative embodiments illustrated in FIGS. 8A-8B, it will be appreciated that an obstruction could also fall between the illumination assembly 60 and tracker 56 such that the presence of such an obstruction would likewise result in the user not being able to observe light reflected by the reflective feature 82 of the tracker 56, which nevertheless similarly communicates to the user a change in the status condition SC of the tracker 56 and/or a change in the system condition MC of the surgical system 30. Here, it will be appreciated that this illustrative scenario may be achieved in embodiments where the illumination assembly 60 is arranged generally adjacent to the localizer 54 (e.g., as is depicted in FIGS. 8A-8B) in that interrupting line-of-sight visibility LV of the tracker 56 (e.g., a line-of-sight obstruction LO) would generally also correspond to interrupting light directed at the tracker 56 via the illumination assembly 60. Here, and irrespective of the relative arrangement between the localizer 54 and the illumination assembly 60, it will be appreciated that a change in how light is observed (or not observed) at the reflective feature 82 can prompt the user to further investigate a change in the status condition SC of the tracker 56 and/or the system condition MC of the surgical system 30 (e.g., by observing messages on an output device 68 of a user interface 66 to differentiate between different error types).

Figure 8C:
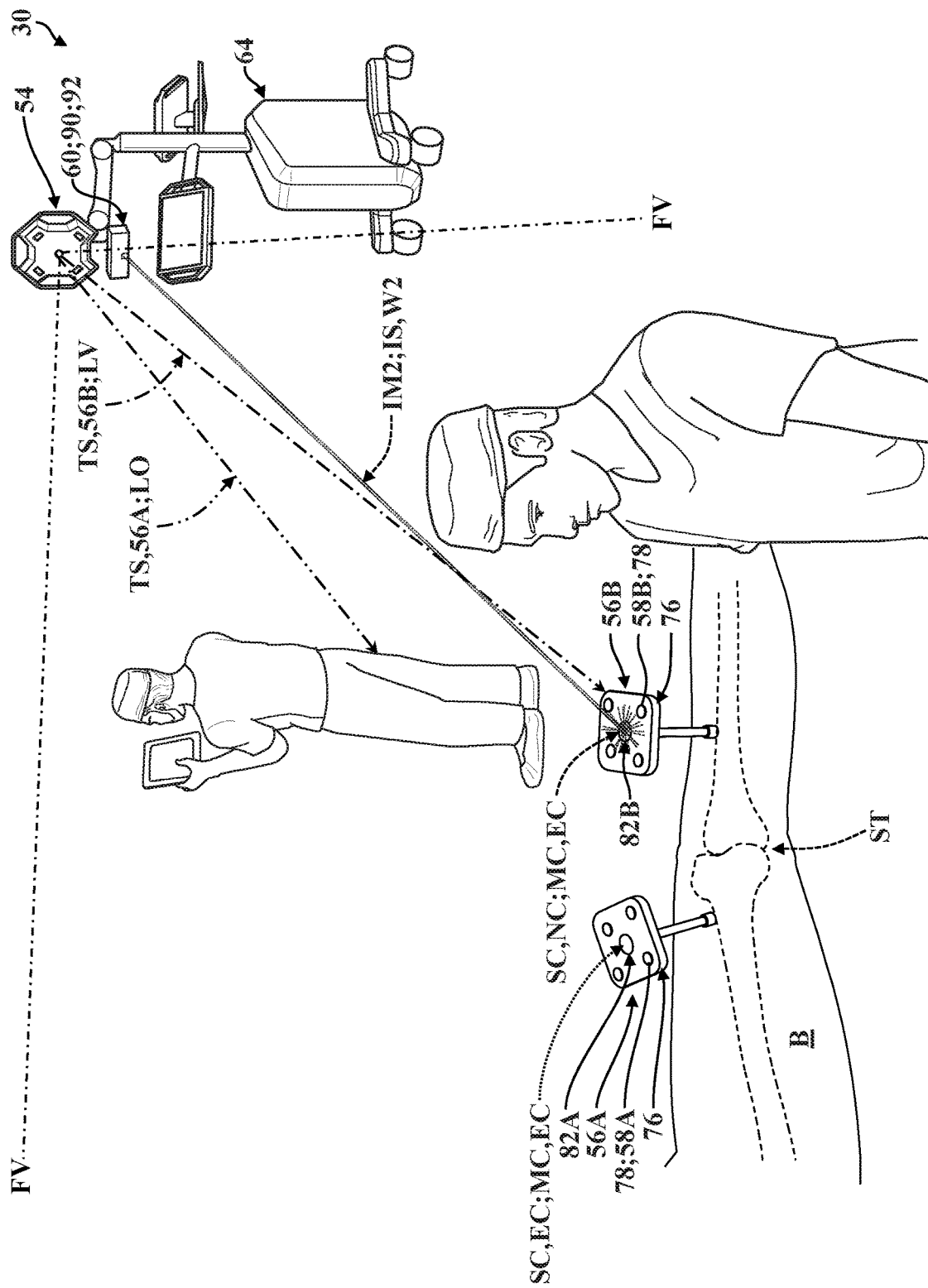
FIG. 8C is another partial perspective view of the navigation system of FIG. 8B, shown with the caregiver still interrupting line-of-sight between the localizer and the first tracker, with the illumination assembly still having interrupted directing light at the first tracker, and with the illumination assembly directing light at the second tracker in a second illumination mode to communicate an error condition to the user.

Continuing to FIG. 8C from FIG. 8A, similar to as was described above in connection with FIG. 8B, the caregiver is shown arranged between the first patient tracker 56A and the localizer 54 to define a line-of-sight obstruction LO. However, in FIG. 8C, the illumination assembly 60 is shown directing light at the second patient tracker 56B emitted at the second wavelength W2 (indicated by a double dashed line) as opposed to at the first wavelength W1 (indicated in FIGS. 8A-8B by a single dashed line). Here, the controller 52 has determined the system condition MC of the navigation system 48 to be in an error condition EC based on at least one of the trackable features 58 of a monitored tracker 56 (here, the first trackable feature 58A of the first patient tracker 56A) having a status condition SC that is something other than the normal condition NC (e.g., based on the tracked states TS of each of the trackers 56 within the field of view FV).

Comparing FIG. 8C with FIG. 8A demonstrates how the navigation system 48 can be utilized in a number of different ways to communicate status conditions SC of individual trackers 56, as well as to communicate system conditions MC of the navigation system 48 and/or surgical system 30. Because the second patient tracker 56B is reflecting light emitted by the illumination assembly 60 at the second wavelength W2 and was previously reflecting light emitted by the illumination assembly 60 at the first wavelength W1, the user can readily appreciate that the status condition SC of the second patient tracker 56B is the normal condition NC by observing light reflected by the second reflective feature 82B, but can also readily appreciate that the change in wavelength of the reflected light corresponds to a change in the system condition MC from the normal condition NC to the error condition EC. Put differently, observing the change from the first wavelength W1 to the second wavelength W2 via the second reflective feature 82B of the second patient tracker 56B simultaneously communicates to the user that the second patient tracker 56B itself is operating properly in the normal condition NC, but one of the other trackers 56 is obstructed from view of the localizer 54 and is in an error condition EC. Similar to the example described above in connection with FIG. 8B, the user can likewise observe that the first patient tracker 56A is not reflecting any light and was previously (see FIG. 8A), and can readily appreciate that the status condition SC of the first patient tracker 56A has changed to the error condition EC based on the absence of light reflected by the first reflected feature 82A.

Figure 9A:
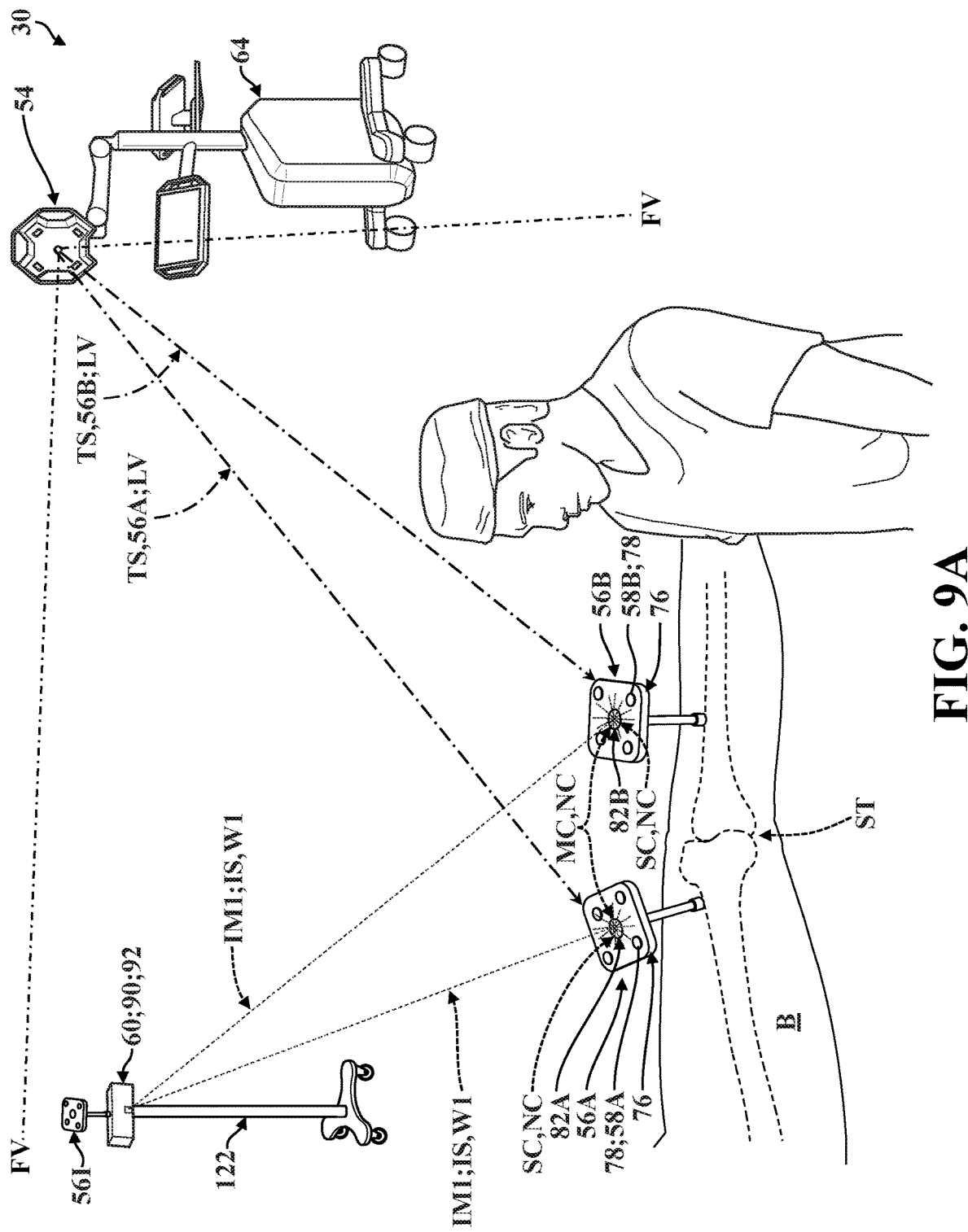
FIG. 9A is a partial perspective view of the navigation system of FIG. 1, shown with first and second trackers coupled to respective portions of the patient's body adjacent to the surgical site, and shown with an illumination assembly spaced from a localizer and directing light at each of the first and second trackers to communicate a normal condition for each of the first and second trackers.

Referring now to FIG. 9A, another example of the surgical system 30 with a navigation system 48 according to the present disclosure is shown with a patient undergoing a surgical procedure. Here too, similar to the example described above in connection with FIG. 8A, the surgical site ST is defined by the patient's right knee joint, and first and second patient trackers 56A, 56B are attached to adjacent bones of the patient's body B (e.g., the femur and the tibia) and are arranged within the field of view FV of the localizer 54. The user (e.g., a surgeon) is able to readily observe the first and second patient trackers 56A, 56B adjacent to the surgical site ST which likewise comprise respective first and second trackable features 58A, 58B as well as respective first and second reflective features 82A, 82B.

However, in the example illustrated in FIG. 9A, the illumination assembly 60 is spaced from the localizer 54 and is operatively attached to a mobile stand 122 that can be moved relative to other components of the surgical system 30. This arrangement allows the controller 52 to direct light emitted by the illumination assembly 60 within the field of view FV of the localizer 54 in different ways, and can afford additional functionality in certain applications, as described in greater detail below. Here, because the illumination assembly 60 is coupled to the mobile stand 122, the position and orientation of the illumination assembly 60 is determined by the localizer 54 via the trackable feature 58 of the illumination assembly tracker 56I, and the controller 52 can communicate with the illumination assembly 60 via wired or wireless communication to facilitate operation of the light module 90 and/or aiming unit 92, as noted above. In some embodiments, the illumination assembly 60 is spaced from the localizer 54 and is operatively attached to the surgical robot 32 (not shown), such that the position and orientation of the illumination assembly 60 can be determined by the navigation system 48, such as based on the arrangement of the illumination assembly 60 relative to the base 34 of the surgical robot 32, based on the kinematics of the robotic arm 36 and known fixed relationships between the illumination assembly 60 and one or more rigid reference points on the surgical robot 32 and/or end effector 40, and the like. Other configurations are contemplated.

In FIG. 9A, like FIG. 8B described above, the localizer 54 has line-of-sight visibility LV (indicated by dash-dot lines) with each of the first and second patient trackers 56A, 56B. Here too, based on visibility between the localizer 54 and the first and second trackable features 58A, 58B of the respective first and second patient trackers 56A, 56B, the controller 52 determines that the status conditions SC of each of the first and second patient trackers 56A, 56B are normal conditions NC. Accordingly, the controller 52 operates the illumination assembly 60 in the first illumination mode IM1 to direct light at both the first patient tracker 56A and the second patient tracker 56B in order to communicate the normal conditions NC to the user. Thus, light reflected by the first and second reflective features 82A, 82B can be readily observed by the user to communicate the status conditions SC (here, normal conditions NC) of each of the first and second patient trackers 56A, 56B. Here too, the controller 52 determines that the system condition MC of the navigation system 48 is likewise in a normal condition NC, which in this example may be communicated to the user based on light being reflected at the same wavelength W1 by each of the first and second patient trackers 56A, 56B.

Figure 9B:
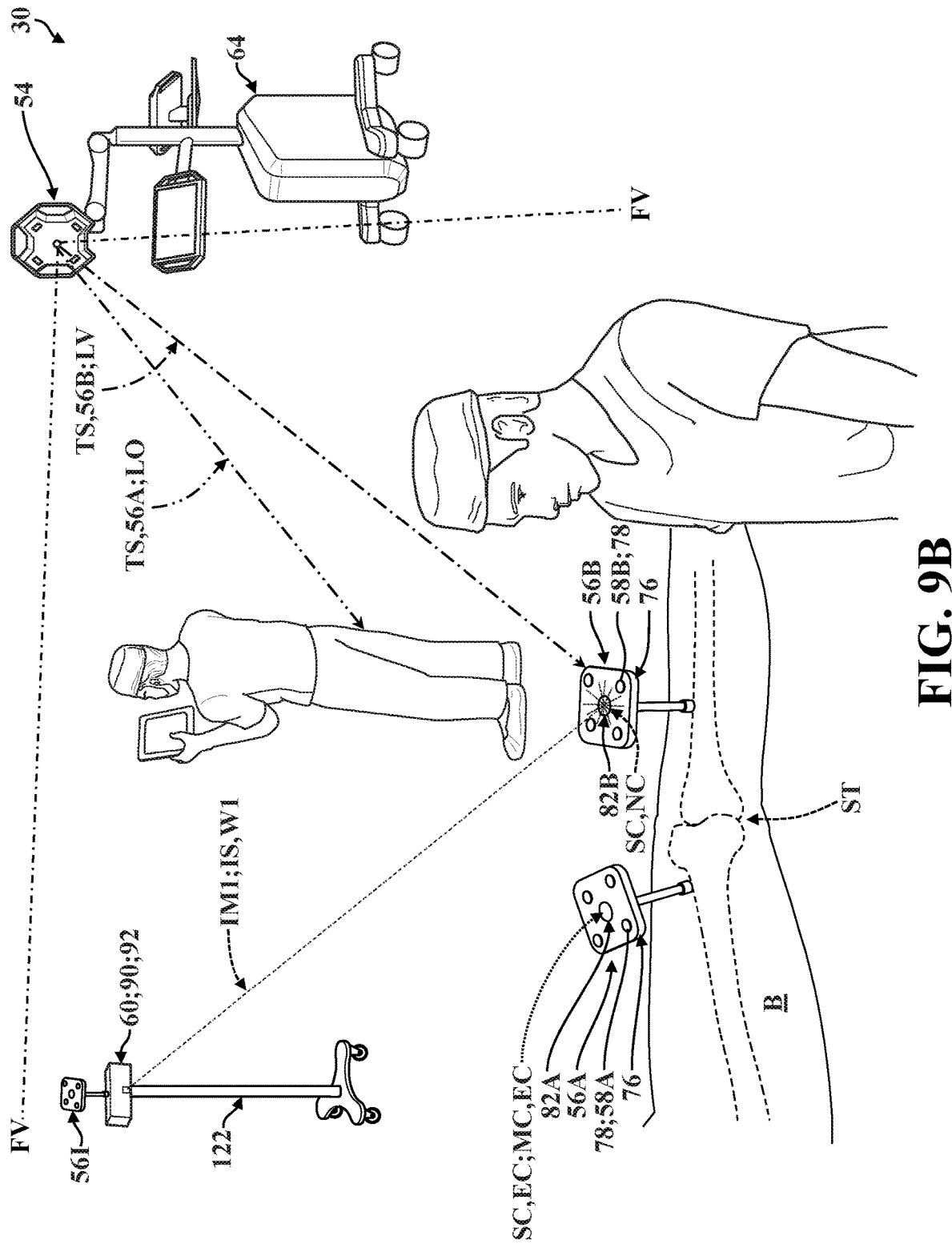
FIG. 9B is another partial perspective view of the navigation system of FIG. 9A, shown with a caregiver interrupting line-of-sight between the localizer and the first tracker, with the illumination assembly having interrupted directing light at the first tracker to communicate an error condition to a user, and with the illumination assembly directing light at the second tracker in a first illumination mode to communicate the normal condition for the second tracker.

Continuing now to FIG. 9B from FIG. 9A, a caregiver is shown arranged between the localizer 54 and the first patient tracker 56A. Here, similar to the scenario described above in connection with FIG. 8B, while the localizer 54 still has line-of-sight visibility LV (indicated by a dash-dot line) with the second trackable feature 58B of the second patient tracker 56B, there is a line-of-sight obstruction LO (indicated by a dash-dot-dot line) with the first trackable feature 58A of the first patient tracker 56A caused by the caregiver. Accordingly, the controller 52 determines that the status condition SC of the second patient tracker 56B is the normal condition NC based on visibility of the second trackable feature 58B, and determines that the status condition SC of the first patient tracker 56A is an error condition EC based on obstruction of the first trackable feature 58A. Here too, the controller 52 operates the illumination assembly 60 to direct light at the second reflective feature 82B in order to communicate the normal condition NC of the second patient tracker 56B, but does not direct light at the first reflective feature 82A in order to communicate the error condition EC of the first patient tracker 56A. Put differently, the controller 52 operates the illumination assembly 60 in the first illumination mode IM1 for the second patient tracker 56B, and operates the illumination assembly 60 in the second illumination mode IM2 for the first patient tracker 56A.

Comparing FIG. 9B with FIG. 9A likewise demonstrates how the navigation system 48 can be utilized to communicate status conditions SC of individual trackers 56. Because the second patient tracker 56B is reflecting light emitted by the illumination assembly 60 at the first wavelength W1 (indicated by a single dashed line), but the first patient tracker 56A is not reflecting any light and was previously (compare FIG. 9B to FIG. 9A), the user can readily appreciate that the status condition SC of the second patient tracker 56B is the normal condition NC by observing light at the first wavelength W1 reflected by the second reflective feature 82B, and also that the status condition SC of the first patient tracker 56A has changed to the error condition EC by observing the absence of light reflected by the first reflected feature 82A.

Figure 9C:
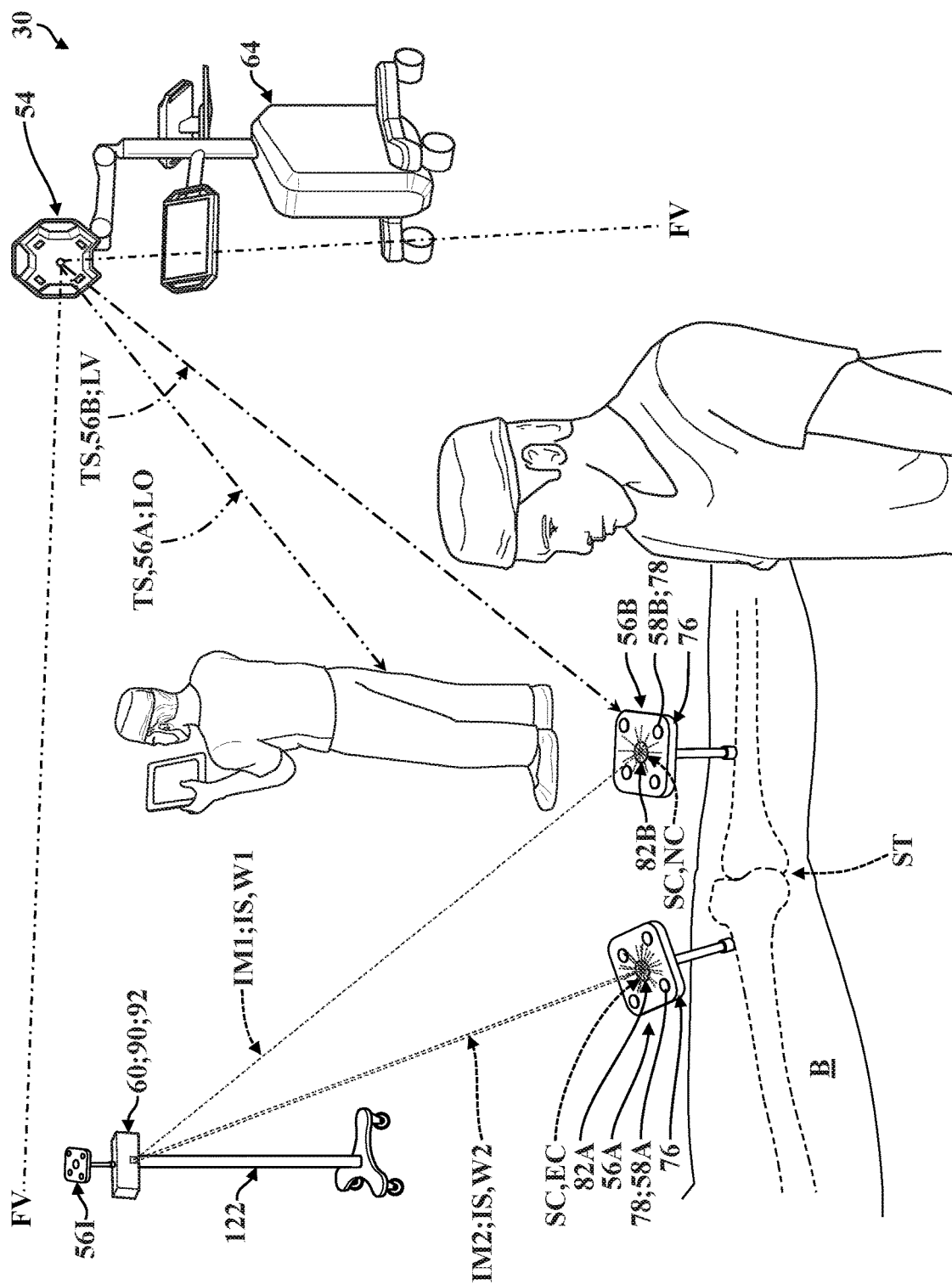
FIG. 9C is another partial perspective view of the navigation system of FIG. 9B, shown with the caregiver still interrupting line-of-sight between the localizer and the first tracker, with the illumination assembly directing light at the second tracker in a first illumination mode to communicate the normal condition for the second tracker, and with the illumination assembly directing light at the first tracker in a second illumination mode to communicate an error condition for the first tracker.

Continuing to FIG. 9C from FIG. 9A, similar to as was described above in connection with FIGS. 9B and 8B, the caregiver is shown arranged between the first patient tracker 56A and the localizer 54 to define a line-of-sight obstruction LO. However, in FIG. 9C, the illumination assembly 60 is shown operating in the second illumination mode IM2 directing light toward the first patient tracker 56A at the second wavelength W2 (indicated by a double dashed line), and in the first illumination mode IM1 directing light toward the second patient tracker 56B at the first wavelength W1 (indicated by a single dashed line). This configuration is achieved based on the spaced arrangement of the illumination assembly 60 relative to the localizer 54; here in this illustrative example, while the line-of-sight obstruction LO created by the caregiver affects the localizer's 54 ability to monitor tracked states TS of the first patient tracker 56A in real time, the illumination assembly 60 is not presented with an obstruction and can still emit light toward the first patient tracker 56A. Thus, the controller 52 may be configured to direct light towards the first patient tracker 56A based on the last known position of the first reflective feature 82A prior to the localizer 54 determining the presence of an obstruction of the first trackable feature 58A. However, other configurations are contemplated, and the controller 52 could be configured to estimate or otherwise determine the location of the first patient tracker 56A in other ways (e.g., with additional localizers, imaging systems, inertial sensors, and the like). Other configurations are contemplated.

Irrespective of how the location of the first patient tracker 56A illustrated in FIG. 9C is approximated or otherwise determined, as noted above, the illumination assembly 60 is depicted operating in the second illumination mode IM2 with an illumination state IS defined by light emission at the second wavelength W2 (indicated by a double dashed line) directed at the first patient tracker 56A, and operating in the first illumination mode IM1 with an illumination state IS defined by light emission at the first wavelength W1 (indicated by a single dashed line) directed at the second reflective feature 82B of the second patient tracker 56B. TO this end, the illumination assembly 60 depicted in FIG. 9D may be configured similar to the example described above in connection with FIGS. 7A-7D. However, other configurations are contemplated.

Comparing FIG. 9C with FIG. 9A demonstrates how the navigation system 48 can be utilized in a number of different ways to communicate status conditions SC of individual trackers 56, as well as to communicate system conditions MC of the navigation system 48 and/or surgical system 30. Because the first patient tracker 56A is reflecting light emitted by the illumination assembly 60 at the second wavelength W2 and was previously reflecting light emitted by the illumination assembly 60 at the first wavelength W1, the user can readily appreciate that the change in wavelength of the reflected light corresponds to a change in the status condition SC from the normal condition NC to the error condition EC. Furthermore, because the second patient tracker 56B continues to reflect light emitted by the illumination assembly 60 at the first wavelength W1, the user can readily appreciate that the first patient tracker 56A remains in the normal condition NC. In some examples, the controller 52 could also be configured to operate the illumination assembly 60 so as to emit light at the second wavelength W2 toward both the first and second patient trackers 56A, 56B in some examples (not shown), such as to communicate a change in the system condition MC to the user. Other configurations are contemplated.

Figure 10A:
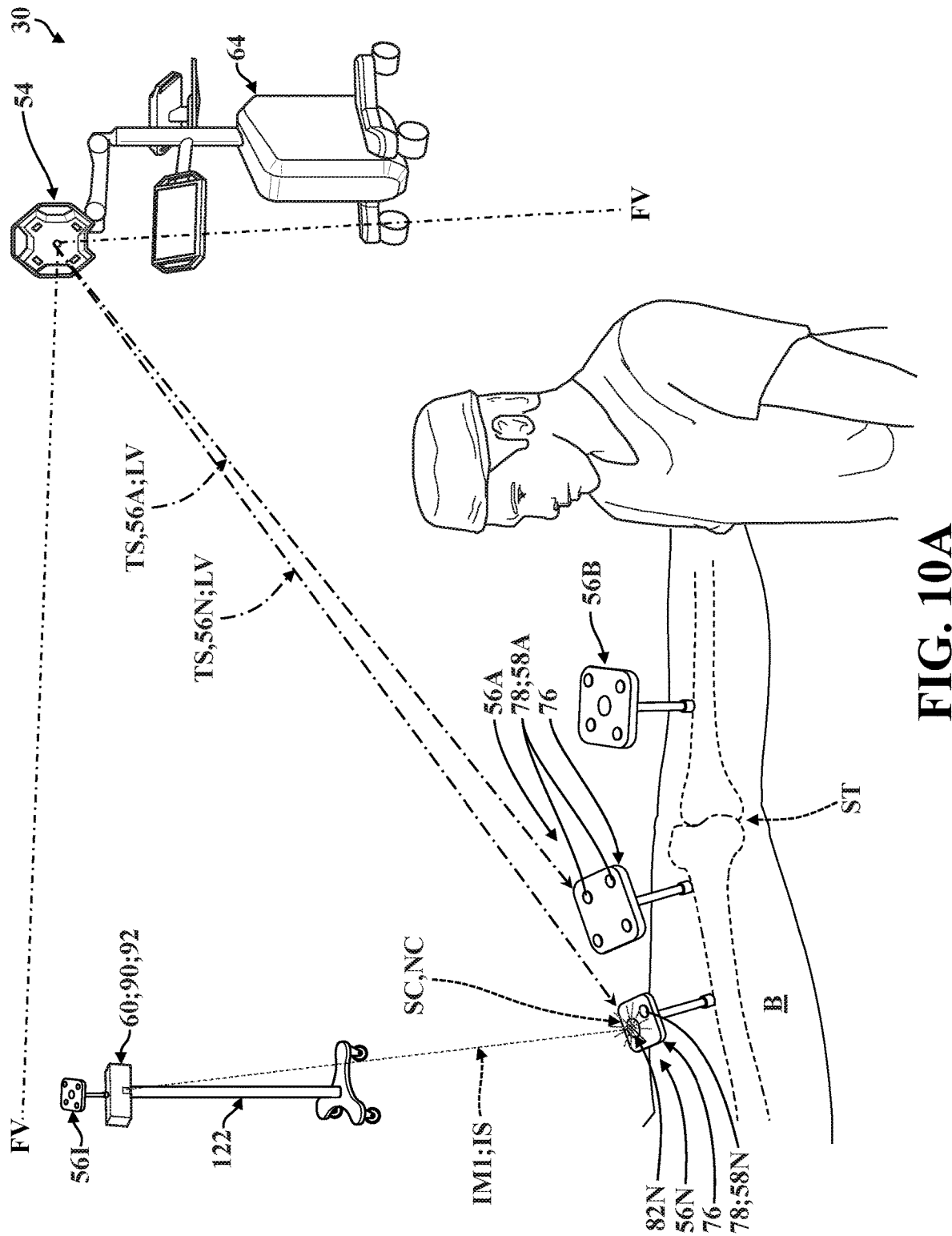
FIG. 10A is a partial perspective view of the navigation system of FIG. 1, shown with a first patient tracker and an ancillary patient tracker coupled to the same portion of the patient's body adjacent to the surgical site, and shown with an illumination assembly spaced from a localizer and directing light at the ancillary patient tracker to communicate a normal condition for the first patient tracker.

Referring now to FIG. 10A, another example of the surgical system 30 with a navigation system 48 according to the present disclosure is shown with a patient undergoing a surgical procedure. Here too, similar to the example described above in connection with FIG. 9A, the surgical site ST is defined by the patient's right knee joint, and first and second patient trackers 56A, 56B are attached to adjacent bones of the patient's body B (e.g., the femur and the tibia) and are arranged within the field of view FV of the localizer 54. The user (e.g., a surgeon) is able to readily observe the first and second patient trackers 56A, 56B adjacent to the surgical site ST which likewise comprise respective first and second trackable features 58A, 58B.

However, in the example illustrated in FIG. 10A, while the navigation system 48 is configured to track states TS of each tracker 56 within the field of view FV, the second patient tracker 56B is inactive for illustrative purposes (e.g., to represent a surgical procedure that only utilizes the second patient tracker 56B during some of the workflow). Furthermore, in the representative embodiment illustrated in FIG. 10A, the first patient tracker 56A does not comprise a reflective feature 82, and an ancillary patient tracker 56N is shown attached to the same portion of the patient's body B as the first patient tracker 56A (e.g., the femur) such that the first patient tracker 56A and the ancillary patient tracker 56N move concurrently. However, it will be appreciated that the first patient tracker 56A and/or the ancillary patient tracker 56N may each be illuminated in some embodiments, irrespective of whether or not each employs a reflective feature 82. To this end, the first patient tracker 56A may be illuminated to identify a normal condition NC, and the ancillary marker 56N can be illuminated to communicate that ancillary/redundant tracking is active. Other configurations are contemplated. In the representative embodiment illustrated in FIG. 10A, the ancillary patient tracker 56N comprises a trackable feature 58N defined by a passive marker 78 that can be monitored by the navigation system 48, and also comprises a reflective feature 82N. With this configuration, the navigation system 48 is configured to track states TS of the first and ancillary patient trackers 56A, 56N, and the controller 52 is further configured to relate the tracked states TS of the ancillary patient tracker 56N to the first patient tracker 56A. More specifically, in some configurations, the navigation system 48 may register combined geometry of the first patient tracker 56A and the ancillary patient tracker 56N, and may determine an error when the tracked geometry deviates from the registered geometry. Accordingly, in this embodiment, the controller 52 is configured to operate the illumination assembly 60 to direct light toward the reflective feature 82N of the ancillary patient tracker 56N to communicate the status condition SC of the first patient tracker 56A to the user. However, it will be appreciated that other configurations are contemplated by the present disclosure. In some embodiments, for example, the illumination assembly 60 could direct light toward a reflective feature 82A of a patient tracker 56A and toward a reflective feature 82N of another object that is fixed to the same bone as the patient tracker 56 but is not necessarily monitored actively by the navigation system 48 (e.g., an object that is registered in the localizer coordinate system LCLZ via the pointer tool 62 but does not employ a discrete marker 78). Other configurations are contemplated.

In FIG. 10A, the localizer 54 has line-of-sight visibility LV (indicated by dash-dot lines) with each of the first and ancillary patient trackers 56A, 56N. Here, based on visibility between the localizer 54 and the trackable features 58A, 58N of the respective first and ancillary patient trackers 56A, 56N, the controller 52 determines that the status condition SC of the first patient tracker 56A is the normal condition NC based on an absence of change in the arrangement of the first patient tracker 56A relative to the ancillary patient tracker 56N because of their rigid connection to the same portion of the patient's body B (e.g., the femur). Put differently, because the first and ancillary patient trackers 56A, 56N move concurrently, and the controller 52 will determine that the first patient tracker 56A is in the normal condition NC unless one moves relative to the other. Accordingly, the controller 52 operates the illumination assembly 60 in the first illumination mode IM1 to direct light at the ancillary patient tracker 56N in order to communicate the normal condition NC of the first patient tracker 56A to the user.

Figure 10B:
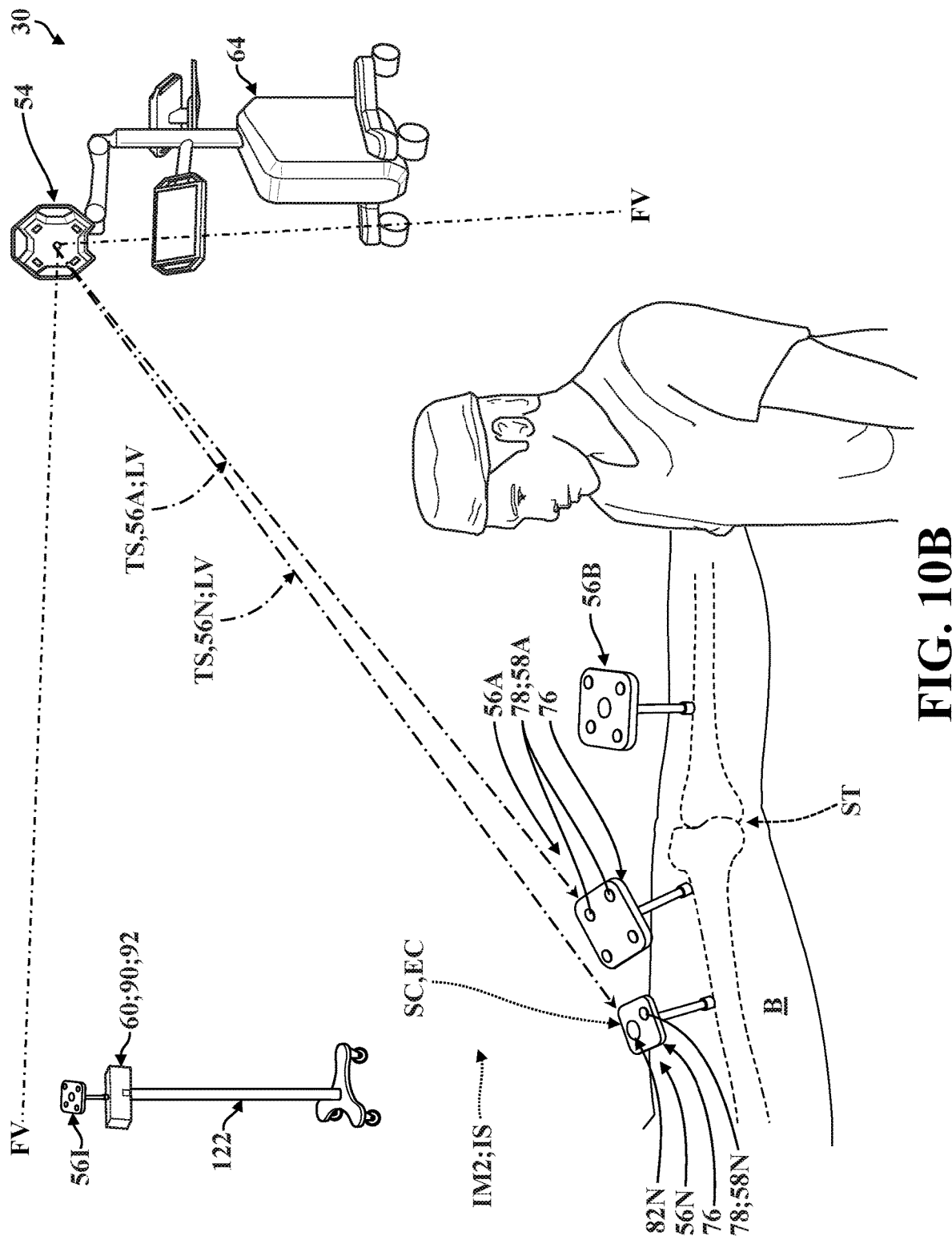
FIG. 10B is another partial perspective view of the navigation system of FIG. 9A, shown with a first patient tracker having moved relative to the ancillary patient tracker and to the portion of the patient's body, and shown with the illumination assembly having interrupted directing light at the ancillary patient tracker to communicate an error condition to a user.

Thus, as depicted in FIG. 10A, light reflected by the reflective feature 82N can be readily observed by the user to communicate the status condition SC (here, the normal condition NC) of the first patient tracker 56A. However, if the first patient tracker 56A inadvertently becomes loose or otherwise changes arrangement relative to the ancillary patient tracker 56N (e.g., as depicted in FIG. 10B; compare with FIG. 10A), the controller 52 determines that the first patient tracker 56A is in the error condition EC. Here, as shown in FIG. 10B, while the localizer 54 still has line-of-sight visibility LV (indicated by a dash-dot line) with the trackable features 58A 58N of the first and ancillary patient trackers 56A, 56N, the controller 52 determines that the status condition SC of the first patient tracker 56A is an error condition EC based on the change in the arrangement between the first and ancillary patient trackers 56A, 56N effected by inadvertent loosening of the first patient tracker 56A described above. Accordingly, in this embodiment, the controller 52 then operates the illumination assembly 60 in the second illumination mode IM2 so as not to direct light at the reflective feature 82N of the ancillary patient tracker 56N in order to communicate the error condition EC of the first patient tracker 56A to the user. However, it will be appreciated that the change in illumination of the reflective feature 82N of the ancillary patient tracker 56N could be communicated to the user based on the illumination assembly 60 directing light away from the reflective feature 82N resulting from misalignment between the first and ancillary patient trackers 56A, 56N. Put differently, the change in illumination of the reflective feature 82N could be communicated to the user without necessarily altering how the illumination assembly 60 itself is operated (e.g., via the controller 52) in scenarios where misalignment between the first and ancillary patient trackers 56A, 56N results in the illumination assembly 60 directing light toward a location other than at the reflective feature 82N (e.g., where the reflective feature 82N would otherwise be located but for the misalignment).

It will be appreciated that the configuration described above in connection with FIGS. 10A-10B affords the ability to utilize ancillary trackers 56N to communicate the status condition SC (and/or system condition MC) of a patient tracker 56A that is attached to the same portion of the patient's body B while ensuring that error conditions EC of various types (e.g., based on inadvertent loosening or misalignment of patient trackers) can be readily communicated to the user via the illumination assembly 60.

It will be appreciated that the illumination assembly 60 can also help facilitate improved accuracy and usability of the navigation system 48 via feedback generated based on how light directed at the trackers 56 from the illumination assembly 60 is observed either by the user or the surgical system 30. By way of non-limiting example, feedback may be utilized to help facilitate optimizing the alignment of the illumination assembly 60 relative to the surgical site ST, the reflective features 82, and/or the localizer 54, either automatically or by user-actuated adjustment. Here, because the illumination assembly 60 can be tracked in the same coordinate system as the trackers 56 (e.g., via utilization of a illumination assembly tracker 561, via coupling to the surgical robot 32 described above, and the like), parameters utilized when adjusting the illumination assembly 60 can be converted into corresponding adjustments in the localizer coordinate system LCLZ to facilitate adjusting and registering tracked states TS of trackers 56 via the navigation system 48. Furthermore, it is contemplated that feedback could be utilized by the navigation system 48 to improve monitoring accuracy (e.g., by prompting the user to verify that a particular tracker 56 is reflecting light from the illumination assembly 60 in a certain way). Thus, in addition to being able to readily discern changes in how light is reflected by the reflective features 82 (e.g., in different colors, between on-and-off, and the like) in order to determine changes in status conditions SC or system conditions MC, the user may be prompted by the surgical system 30 (e.g., via the user interface 66) to confirm that certain types of light can be observed (or not observed) at one or more trackers 56 during specific parts of the surgical procedure workflow. Furthermore, it will be appreciated that feedback can be also be provided to the surgical system 30 automatically, such as by using one or more imaging systems (e.g., visible light-capable computer-vision localizers 54, cameras, sensors, and the like) to observe trackers 56 for reflected visible light directed at the trackers 56 via the illumination assembly 60. Other configurations are contemplated, and it will be appreciated that feedback can be utilized by the surgical system 30 in a number of different ways.

Irrespective of the specific configuration of the tracker 56 and/or localizer 54 utilized in order to facilitate monitoring tracked states TS during a surgical procedure, the navigation system 48 of the present disclosure allows the user to quickly and reliably observe and discern status conditions SC of trackers 56 and/or system conditions MC of the navigation system 48 and/or surgical system 30 without reliance on the power source 88 to facilitate communicating status conditions SC and/or system conditions MC to the user. Put differently, trackers 56 which employ "active" trackable features 58 can be configured without on-board electronics or components dedicated to communicating status conditions SC and/or system conditions MC, thereby allowing utilization of the power source 88 to be optimized for other purposes (e.g., energizing "active" trackable features 58, sensors, and the like). Similarly, trackers 56 with both "active" and "passive" trackable features 58 can be configured according to the present disclosure so as to allow the user to observe status conditions SC and/or system conditions MC without having to look away from the surgical site ST (e.g., to view status information or alerts on a screen or another output device 68). This advantageously affords the user with the ability to quickly and efficiently determine status conditions SC and/or system conditions MC without having to avert attention away from the surgical site ST.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A navigation system comprising:
a tracker having at least one trackable component;
a localizer configured to track states of the at least one trackable component within a field of view;
an illumination assembly located remote from the tracker and operable to direct a visible light within the field of view; and
a controller coupled to the localizer and to the illumination assembly and the controller being configured to:
receive the tracked states from the localizer;
determine a status condition of the tracker based on the tracked states received from the localizer, wherein the status condition identifies whether or not the tracker is being properly detected by the localizer; and
control the illumination assembly to remotely direct the visible light at the tracker such that the visible light reflected by the tracker from the illumination assembly is visible to a user of the navigation system to communicate the status condition of the tracker.

2. The navigation system of claim 1, wherein:
the tracker comprises a reflective indicator being separate from the at least one the trackable component and being configured to reflect the visible light; and
the controller is further configured to control the illumination assembly to remotely direct the visible light at the reflective indicator such that the visible light reflected by the reflective indicator from the illumination assembly is visible to the user of the navigation system to communicate the status condition of the tracker.

3. The navigation system of claim 1, wherein:
the illumination assembly comprises a light module operable to emit the visible light;
the illumination assembly is operable between a first illumination mode to emit the visible light, and a second illumination mode different from the first illumination mode; and
wherein the controller is further configured to:
operate the illumination assembly in the first illumination mode in response to determining that the status condition indicates visibility between the localizer and the at least one trackable component; and
operate the illumination assembly in the second illumination mode in response to determining that the status condition indicates obstruction between the localizer and the at least one trackable component.

4. The navigation system of claim 3, wherein the second illumination mode comprises an illumination state defined by an absence of visible light emission.

5. The navigation system of claim 3, wherein:
the first illumination mode comprises an illumination state defined by visible light emission at a first wavelength; and
the second illumination mode comprises an illumination state defined by visible light emission at a second wavelength different from the first wavelength.

6. The navigation system of claim 1, wherein the tracker is further defined as a first tracker having at least one first trackable component; and further comprising a second tracker having at least one second trackable component;
wherein the localizer is further configured to track states of the at least one second trackable component within the field of view; and
wherein the controller is further configured to:
determine the status condition of the second tracker based on the tracked states received from the localizer; and
control the illumination assembly to remotely direct the visible light at the second tracker such that the visible light reflected by the second tracker from the illumination assembly is visible to the user to communicate the status condition of the second tracker.

7. The navigation system of claim 6, wherein the controller is further configured to control the illumination assembly to remotely scan the visible light sequentially between the first tracker and the second tracker.

8. The navigation system of claim 6, wherein:
the illumination assembly comprises a light module operable between a first illumination mode to emit the visible light at a first wavelength, and a second illumination mode to emit the visible light at a second wavelength different from the first wavelength; and
the controller is further configured to control the illumination assembly to remotely direct the visible light emitted by the light module in the first illumination mode at one or more of the first tracker and the second tracker such that the visible light at the first wavelength reflected by one or more of the first tracker and the second tracker is visible to the user to communicate the status condition of one or more of the first tracker and the second tracker.

9. The navigation system of claim 1, wherein the controller is further configured to:
determine a system condition of the navigation system based on the tracked states received from the localizer; and
control the illumination assembly to remotely direct the visible light at the tracker such that the visible light reflected by the tracker from the illumination assembly is visible to the user of the navigation system to communicate the system condition of the navigation system.

10. The navigation system of claim 1, wherein the illumination assembly comprises:
a light module operable to emit the visible light; and
an aiming unit arranged to direct the visible light emitted by the light module within the field of view.

11. The navigation system of claim 10, wherein the aiming unit comprises:
a first actuator assembly operable to direct the visible light emitted by the light module in a first direction within the field of view, and
a second actuator assembly operable to direct the visible light emitted by the light module in a second direction within the field of view, with the second direction being different from the first direction.

12. The navigation system of claim 11, wherein:
the first actuator assembly comprises a first rotary actuator with a first shaft arranged for movement about a first axis;
the second actuator assembly comprises a second rotary actuator with a second shaft arranged for movement about a second axis different from the first axis; and
the aiming unit further comprises a mirror operatively attached to the first shaft of the first rotary actuator for movement about the first axis relative to the light module to direct the visible light emitted by the light module in the first direction within the field of view.

13. The navigation system of claim 12, wherein:
the mirror is further defined as a first mirror; and
the aiming unit further comprises a second mirror operatively attached to the second shaft of the second rotary actuator for movement about the second axis relative to the light module to direct the visible light emitted by the light module in the second direction within the field of view; and
the second mirror is arranged between the first mirror and the light module such that the visible light emitted by the light module is reflected from the second mirror to the first mirror.

14. The navigation system of claim 1, wherein:
the illumination assembly is spaced apart from and separated from the localizer; and
the illumination assembly further comprises an illumination assembly tracker with a trackable component; and
wherein the localizer is further configured to track states of the trackable component of the illumination assembly tracker.

15. The navigation system of claim 1, wherein the at least one trackable component of the tracker is further defined as at least one passive marker configured to be monitored by the localizer without a power source coupled to the tracker.

16. A surgical system comprising:
a tracker having at least one trackable component and a reflective indicator;
a localizer configured to track states of the at least one trackable component;
an illumination assembly located remote from the tracker and operable to direct a visible light; and
a controller coupled to the localizer and to the illumination assembly and the controller being configured to:
receive the tracked states from the localizer;
determine a status condition of the tracker based on the tracked states received from the localizer, wherein the status condition identifies whether or not the tracker is being properly detected by the localizer; and
control the illumination assembly to remotely direct the visible light at the reflective indicator of the tracker such that the reflective indicator reflects the visible light to visibly communicate the status condition of the tracker to a user.

17. A method of operating a navigation system comprising a tracker having at least one trackable component, a localizer configured to track states of the at least one trackable component within a field of view, an illumination assembly located remote from the tracker and operable to direct a visible light within the field of view, and a controller coupled to the localizer and to the illumination assembly and the controller being configured to perform the steps of:
receiving the tracked states from the localizer;
determining a status condition of the tracker based on the tracked states received from the localizer, the status condition identifying whether or not the tracker is being properly detected by the localizer; and
controlling the illumination assembly for remotely directing the visible light at the tracker such that the visible light reflected by the tracker from the illumination assembly is visible to a user of the navigation system for communicating the status condition of the tracker.

18. The method of claim 17, wherein:

the tracker comprises a reflective indicator being separate from the at least one trackable component; and comprising the controller controlling the illumination assembly for remotely directing the visible light at the reflective indicator such that the reflective indicator reflects the visible light to visibly communicate the status condition of the tracker.

19. The method of claim 17, wherein:

the illumination assembly comprises a light module operable to emit the visible light;

the illumination assembly is operable between a first illumination mode to emit the visible light, and a second illumination mode different from the first illumination mode; and and comprising the controller:

operating the illumination assembly in the first illumination mode in response to determining that the status condition indicates visibility between the localizer and the at least one trackable component; and operating the illumination assembly in the second illumination mode in response to determining that the status condition indicates obstruction between the localizer and the at least one trackable component.

20. The method of claim 17, comprising the controller:

determining a system condition of the navigation system based on the tracked states received from the localizer; and controlling the illumination assembly for remotely directing the visible light at the tracker such that the visible light reflected by the tracker from the illumination assembly is visible to the user of the navigation system to communicate the system condition of the navigation system.

\* \* \* \* \*